(12) United States Patent
Fish et al.

(10) Patent No.: US 7,122,683 B2
(45) Date of Patent: Oct. 17, 2006

(54) AMIDES USEFUL AS MONOAMINE RE-UPTAKE INHIBITORS

(75) Inventors: Paul Vincent Fish, Sandwich (GB); Thomas Ryckmans, Sandwich (GB); Alan Stobie, Sandwich (GB); Florian Wakenhut, Sandwich (GB); Gavin Alistair Whitlock, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 11/280,128

(22) Filed: Nov. 15, 2005

(65) Prior Publication Data

US 2006/0111429 A1 May 25, 2006

Related U.S. Application Data

(60) Provisional application No. 60/647,534, filed on Jan. 26, 2005.

(30) Foreign Application Priority Data

Nov. 23, 2004 (GB) .................................. 0425766.3

(51) Int. Cl.
*C07D 207/14* (2006.01)
(52) U.S. Cl. ...................................... 548/557
(58) Field of Classification Search ................. 548/557
See application file for complete search history.

(56) References Cited

U.S. PATENT DOCUMENTS 3,577,440 A * 5/1971 Lunsford et al. ........... 548/557

FOREIGN PATENT DOCUMENTS

| CL | 628885 | 1/1978 |
|---|---|---|
| WO | WO 2004110995 | 12/2004 |
| WO | WO 2004111003 | 12/2004 |
| WO | WO 2005047251 | 5/2005 |

OTHER PUBLICATIONS

Norman, Trevor, R., et al., *New Pharmacological Approaches to the Management of Depression: From Theory to Clinical Practice;* Australian and New Zealand Journal of Psychiatry, 1992, 26:73-81.

* cited by examiner

*Primary Examiner*—Kamal A. Saeed
*Assistant Examiner*—Shawquia Young
(74) *Attorney, Agent, or Firm*—Gregg C Benson; Carl J. Goddard

(57) ABSTRACT

A compound of Formula (I)

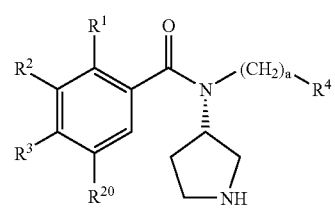

and pharmaceutically and/or veterinarily acceptable derivatives thereof, wherein:

$R^1$, $R^2$, $R^3$ and $R^{20}$ are each independently H, Cl, Br, F, I, $CF_3$, $OCF_3$, Me or Et;

$R^4$ is het or $C_{3-7}$ cycloalkyl optionally substituted by $C_{1-4}$ alkyl, $C_{1-4}$ alkoxy, alkoxyalkyl containing 2 to 4 carbon atoms or —S—($C_{1-4}$ alkyl);

a is 0 or 1; and het is a non-aromatic 4-, 5- or 6-membered heterocycle which contains at least one N, O or S heteroatom, optionally fused to a 5- or 6-membered carbocyclic group or a second 4-, 5- or 6-membered heterocycle which contains at least one N, O or S heteroatom, wherein the het group is optionally substituted by at least one substituent independently selected from $C_{1-8}$alkyl, $C_{1-8}$alkoxy, OH, halo, $CF_3$, $OCF_3$, $SCF_3$, hydroxy-$C_{1-6}$alkyl, $C_{1-4}$alkoxy-$C_{1-6}$alkyl and $C_{1-4}$alkyl-S—$C_{1-4}$alkyl; provided that at least one of $R^1$, $R^2$ and $R^3$ are other than H. The compounds of the invention exhibit activity as both serotonin and noradrenaline re-uptake inhibitors and therefore have utility in a variety of therapeutic areas, for example urinary incontinence.

12 Claims, No Drawings

AMIDES USEFUL AS MONOAMINE RE-UPTAKE INHIBITORS

This application claims priority to U.S. Provisional Application Ser. No. 60/647,534, filed Jan. 26, 2005, which claims priority to UK Application Serial No. 0425766.3, filed Nov. 23, 2004.

This invention relates to novel amide compounds which inhibit monoamine re-uptake, to processes for their preparation, to pharmaceutical compositions containing them and to their use in medicine.

The compounds of the invention exhibit activity as serotonin and/or noradrenaline re-uptake inhibitors and therefore have utility in a variety of therapeutic areas. For example, the compounds of the invention are of use in the treatment of disorders in which the regulation of monoamine transporter function is implicated, more particularly disorders in which inhibition of re-uptake of serotonin or noradrenaline is implicated. Furthermore, the compounds of the invention are of use in disorders in which inhibition of both serotonin and noradrenaline is implicated, such as urinary incontinence. Additionally, the compounds of the invention are of use in disorders in which it may be desired to inhibit preferentially the reuptake of one of noradrenaline or serotonin compared with the other, such as pain, fibromyalgia, ADHD and depression.

According to a first aspect, the invention provides a compound of formula (I),

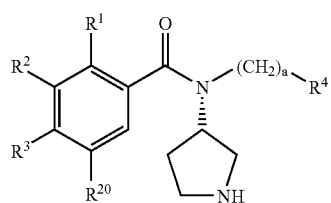

I and pharmaceutically and/or veterinarily acceptable derivatives thereof, wherein:
$R^1$, $R^2$, $R^3$ and $R^{20}$ are each independently H, Cl, Br, F, I, $CF_3$, $OCF_3$, Me or Et;
$R^4$ is het or $C_{3-7}$ cycloalkyl, optionally substituted by $C_{1-4}$ alkyl, $C_{1-4}$ alkoxy, alkoxyalkyl containing 2 to 4 carbon atoms, or —S—($C_{1-4}$ alkyl);
a is 0 or 1; and
het is a non-aromatic 4-, 5- or 6-membered heterocycle which contains at least one N, O or S heteroatom, optionally fused to a 5- or 6-membered carbocyclic group or a second 4-, 5- or 6-membered heterocycle which contains at least one N, O or S heteroatom, wherein the het group is optionally substituted by at least one substituent independently selected from $C_{1-8}$alkyl, $C_{1-8}$alkoxy, OH, halo, $CF_3$, $OCF_3$, $SCF_3$, hydroxy-$C_{1-6}$alkyl, $C_{1-4}$alkoxy-$C_{1-6}$alkyl and $C_{1-4}$alkyl-S—$C_{1-4}$alkyl; provided that at least one of $R^1$, $R^2$ and $R^3$ is other than H.

In an embodiment of the invention, $R^1$ is Cl, Br, F, I, $CF_3$, Me or Et; and $R^2$ and $R^3$ are each independently H, Cl, Br, F, I, $CF_3$, Me or Et. In a further embodiment, $R^1$ and $R^2$ are each independently Cl, Br, F, I, $CF_3$, Me or Et and $R^3$ is H, Cl, Br, F, I, $CF_3$, Me or Et. In a still further embodiment, $R^1$ is Cl, Me or $CF_3$; $R^2$ is H, Cl or F; and $R^3$ is H, Cl or F.

According to a further embodiment of the invention, $R^2$ and $R^{20}$ are other than H. In such an embodiment, $R^2$ and $R^{20}$ may each be independently Cl, F, $CF_3$, Me or Et.

According to a still further embodiment of the invention, $R^1$, $R^2$ and $R^{20}$ are other than H. In such an embodiment, $R^1$, $R^2$ and $R^{20}$ may each be independently Cl, F, $CF_3$, Me or Et.

According to a yet further embodiment of the invention, $R^1$, $R^3$ and $R^{20}$ are other than H. In such an embodiment, $R^1$, $R^3$ and $R^{20}$ may each be independently Cl, F, $CF_3$, Me or Et.

According to any embodiment of the invention described above, $R^4$ may be $C_{3-7}$ cycloalkyl, optionally substituted by $C_{1-4}$ alkyl, $C_{1-4}$ alkoxy, alkoxyalkyl containing 2 to 4 carbon atoms or —S—($C_{1-4}$ alkyl).

According to a further embodiment, $R^4$ may be $C_{3-7}$ cycloalkyl, optionally substituted by Me or Et.

According to any embodiment of the invention described above, a may be 0.

According to any embodiment of the invention described above, the het group may be substituted by one, two or three substituents independently selected from halo, OH, $C_{1-4}$alkyl and $CF_3$. In a further embodiment, the het group of a compound as defined above with reference to the first aspect of the invention and any of the specific embodiments may be unsubstituted.

In a further embodiment, the invention provides a compound selected from:
2,3-dichloro-N-cyclopentyl-N-[(3S)-pyrrolidin-3-yl]benzamide,
2,3-dichloro-N-cyclopentyl-4-fluoro-N-[(3S)-pyrrolidin-3-yl]benzamide,
3-chloro-N-cyclopentyl-2-methyl-N-[(3S)-pyrrolidin-3-yl]benzamide,
N-cyclopentyl-3-fluoro-2-methyl-N-[(3S)-pyrrolidin-3-yl]benzamide,
2-chloro-N-cyclopentyl-3-fluoro-N-[(3S)-pyrrolidin-3-yl]benzamide,
2,3-dichloro-N-cyclohexyl-N-[(3S)-pyrrolidin-3-yl]benzamide,
2-chloro-N-cyclohexyl-3-fluoro-N-[(3S)-pyrrolidin-3-yl]benzamide,
N-cyclohexyl-3-fluoro-2-methyl-N-[(3S)-pyrrolidin-3-yl]benzamide,
2,3-dichloro-N-cyclobutyl-N-[(3S)-pyrrolidin-3-yl]benzamide,
N-cyclobutyl-methyl-2,3-dichloro-N-[(3S)-pyrrolidin-3-yl]benzamide,
2,3-dichloro-N-(cyclopropyl-methyl)-N-[(3S)-pyrrolidin-3-yl]benzamide,
2,3-dichloro-N-[(3S)-pyrrolidin-3-yl]-N-tetrahydro-2H-pyran-4-ylbenzamide,
2-chloro-N-cyclopentyl-N-[(3S)-pyrrolidin-3-yl]benzamide,
2-chloro-N-cyclohexyl-N-[(3S)-pyrrolidin-3-yl]benzamide,
2-chloro-N-cycloheptyl-N-[(3S)-pyrrolidin-3-yl]benzamide,
N-cycloheptyl-N-[(3S)-pyrrolidin-3-yl]-2-(trifluoromethyl)benzamide,
N-cyclohexyl-N-[(3S)-pyrrolidin-3-yl]-2-(trifluoromethyl)benzamide,
N-cyclopentyl-N-[(3S)-pyrrolidin-3-yl]-2-(trifluoromethyl)benzamide,
2,3-Dichloro-N-[(1-methylcyclopropyl)methyl]-N-[(3S)-pyrrolidin-3-yl]benzamide,
3-Chloro-2-methyl-N-[(1-methylcyclopropyl)methyl]-N-[(3S)-pyrrolidin-3-yl]benzamide,
N-(cyclobutylmethyl)-N-[(3S)-pyrrolidin-3-yl]-2-(trifluoromethyl)benzamide,
or pharmaceutically and/or veterinarily acceptable derivatives thereof.

By pharmaceutically and/or veterinarily acceptable derivative it is meant any pharmaceutically or veterinarily acceptable salt, solvate, ester or amide, or salt or solvate of such ester or amide, of the compound of formula (I), or any other compound which upon administration to the recipient is capable of providing (directly or indirectly) a compound of formula (I) or an active metabolite or residue thereof.

For pharmaceutical or veterinary use, the salts referred to above will be the pharmaceutically or veterinarily acceptable salts, but other salts may find use, for example in the preparation of a compounds of formula (I) and the pharmaceutically or veterinarily acceptable salts thereof.

The aforementioned pharmaceutically or veterinarily acceptable salts include the acid addition salts thereof and the base salts thereof.

Suitable acid addition salts are formed from acids which form non-toxic salts. Examples include the acetate, aspartate, benzoate, besylate, bicarbonate/carbonate, bisulphate/sulphate, camsylate, citrate, hemicitrate, edisylate, hemiedisylate, esylate, fumarate, gluceptate, gluconate, glucuronate, hibenzate, hydrochloride/chloride, hydrobromide/bromide, hydroiodide/iodide, isethionate, lactate, malate, maleate, malonate, mesylate, methylsulphate, 2-napsylate, nicotinate, nitrate, orotate, pamoate, phosphate/hydrogen phosphate/dihydrogen phosphate, saccharate, stearate, succinate, tartrate and tosylate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I) may be readily prepared by mixing together solutions of the compound and the desired acid or base, as appropriate. The salt may precipitate from solution and be collected by filtration or may be recovered by evaporation of the solvent. The degree of ionisation in the salt may vary from completely ionised to almost non-ionised.

Pharmaceutically acceptable solvates in accordance with the invention include hydrates and solvates of the compound of formula (I).

Also within the scope of the invention are complexes such as clathrates, drug-host inclusion complexes wherein, in contrast to the aforementioned solvates, the drug and host are present in stoichiometric or non-stoichiometric amounts. Also included in this invention are complexes of the pharmaceutical drug which contain two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269–1288 by Haleblian (August 1975).

The compounds of formula (I) may be modified to provide pharmaceutically or veterinarily acceptable derivatives thereof at any of the functional groups in the compounds. Examples of such derivatives are described in: Drugs of Today, Volume 19, Number 9, 1983, pp 499–538; Topics in Chemistry, Chapter 31, pp 306–316; and in "Design of Prodrugs" by H. Bundgaard, Elsevier, 1985, Chapter 1 (the disclosures in which documents are incorporated herein by reference) and include: esters, carbonate esters, hemi-esters, phosphate esters, nitro esters, sulfate esters, sulfoxides, amides, sulphonamides, carbamates, azo-compounds, phosphamides, glycosides, ethers, acetals and ketals.

It will be further appreciated by those skilled in the art, that certain moieties, known in the art as "pro-moieties", for example as described by H. Bundgaard in "Design of Prodrugs" (ibid) may be placed on appropriate functionalities when such functionalities are present within compounds of the invention.

The compounds of formula (I) contain one or more chiral centres, by virtue of the asymmetric carbon atom of the pyrrolidin-3-yl moiety and further asymmetric carbon atoms as may be defined by certain meanings of $R^4$. Although the stereochemistry at the 3-position is fixed, any further chiral centres may exist in any possible stereoisomeric form.

It is to be understood that the present invention encompasses all isomers of the compounds of the invention, including all geometric, tautomeric and optical forms (with the exception of the chiral centre at the 3-position of the pyrrolidinyl moiety), and mixtures thereof (e.g. tautomeric or racemic mixtures).

The compounds of the invention may exist in one or more tautomeric forms. All tautomers and mixtures thereof are included in the scope of the present invention. For example, a claim to 2-hydroxypyridinyl would also cover its tautomeric form α-pyridonyl.

It is to be understood that the present invention includes radiolabelled compounds of formula (I).

The compounds of formula (I) and their pharmaceutically and veterinarily acceptable derivatives thereof may also be able to exist in more than one crystal form, a characteristic known as polymorphism. All such polymorphic forms ("polymorphs") are encompassed within the scope of the invention. Polymorphism generally can occur as a response to changes in temperature or pressure or both, and can also result from variations in the crystallisation process. Polymorphs can be distinguished by various physical characteristics, and typically the x-ray diffraction patterns, solubility behaviour, and melting point of the compound are used to distinguish polymorphs.

Unless otherwise indicated, any alkyl group may be straight or branched and is of 1 to 8 carbon atoms, such as 1 to 6 carbon atoms or 1 to 4 carbon atoms, for example a methyl, ethyl, n-propyl, i-propyl, n-butyl, i-butyl, s-butyl or t-butyl group. Where the alkyl group contains more than one carbon atom, it may be unsaturated. Thus, the term $C_{1-6}$ alkyl includes $C_{2-6}$ alkenyl and $C_{2-6}$ alkynyl. Similarly, the term $C_{1-8}$ alkyl includes $C_{2-8}$ alkenyl and $C_{2-8}$ alkynyl, and the term $C_{1-4}$ alkyl includes $C_{2-4}$ alkenyl and $C_{2-4}$ alkynyl.

The term halogen is used to represent fluorine, chlorine, bromine or iodine.

Unless otherwise indicated, the term het includes any non-aromatic, saturated or unsaturated 4-, 5- or 6-membered heterocycle which contains up to 4 heteroatoms selected from N, O and S. Examples of such heterocyclic groups included furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, tetrahydropyranyl, pyridyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazapinyl, thiazepinyl, diazepinyl and thiazolinyl. In addition, the term heterocycle includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazdinyl, benzothiazolyl, phthalimido, benzodiazepinyl, indolyl and isoindolyl. The terms het, heterocyclyl and heterocyclic should be similarly construed.

aldehyde $R^4CHO$, followed by reaction with an acid or acid halide as shown (i.e. where X is OH or halo) and deprotection.

Scheme 1

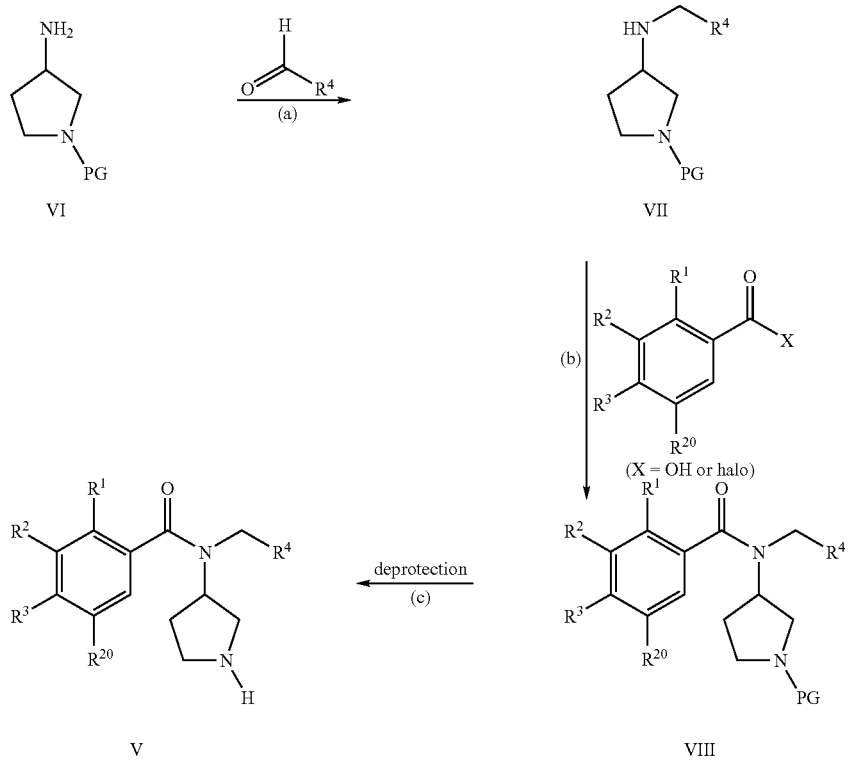

For the avoidance of doubt, unless otherwise indicated, the term substituted means substituted by one or more defined groups. In the case where groups may be selected from a number of alternative groups, the selected groups may be the same or different. Further, the term independently means that where more than one substituent is selected from a number of possible substituents, those substituents may be the same or different.

Hereinafter, the compounds of formula (I), and their pharmaceutically and veterinarily acceptable derivatives, the radiolabelled analogues of the foregoing, the isomers of the foregoing, and the polymorphs of the foregoing, are referred to as "compounds of the invention".

In one embodiment of the invention, the compounds of the invention are the pharmaceutically and veterinarily acceptable derivatives of compounds of formula (I), such as the pharmaceutically or veterinarily acceptable salts or solvates of compounds of formula (I) (e.g. pharmaceutically or veterinarily acceptable salts of compounds of formula (I)).

In a still further embodiment of the invention, there is provided a compound of the invention which is an inhibitor of serotonin and/or noradrenaline monoamine re-uptake, having SRI or NRI Ki values of 200 nM or less. In a further embodiment, the compound has SRI and/or NRI Ki values of 10 nM or less. In a yet further embodiment, the compound has SRI or NRI Ki values of 50 nM or less. In a still further embodiment, the compound has SRI and NRI Ki values of 50 nM or less. In a still yet further embodiment, the compound has SRI and NRI Ki values of 25 nM or less.

According to Scheme 1, compounds of Formula (V) (i.e. a compound of Formula (I) wherein a is 1) may be prepared from compounds of Formula (VI) by reaction with an In the above scheme, $R^1$, $R^2$, $R^3$, $R^4$ and $R^{20}$ are as defined above, a is 1 and PG is a suitable protecting group.

(a)—Reductive Amination

The reaction of the 1° amine (VI) with the aldehyde to form the 2° amine (VII) is a reductive amination reaction, in which the dehydration of the amine and the aldehyde is followed by reduction of the formed imine by a metal hydride reagent or hydrogenation, in a suitable solvent at room temperature.

In this reaction, equimolar amounts of amine and aldehyde are typically treated with either sodium triacetoxyborohydride (STAB), $NaCN(BH)_3$ or $NaBH_4$, in a suitable solvent (e.g. DCM, THF) at room temperature for 1 to 24 hours. Alternatively, an excess of a reducing agent (e.g. $NaBH_4$, $LiAlH_4$, STAB) in a suitable solvent (e.g. THF, MeOH, EtOH) is added after the amine and aldehyde have been mixed for 1–18 hours, optionally in the presence of a drying agent (e.g. molecular sieve) or with the removal of water using Dean-Stark apparatus with a suitable solvent (e.g. toluene, xylene). A further alternative involves catalytic hydrogenation in the presence of a palladium or nickel catalyst (e.g. Pd/C, Raney® Ni) under an atmosphere of $H_2$, optionally at elevated temperature and pressure, in a suitable solvent (e.g. EtOH).

A more specific example of the reductive amination involves treatment of the aldehyde with the amine in the presence of either 10% Pd/C, optionally in the presence of triethylamine, in ethanol under about 415 kPa (about 60 psi)

of hydrogen at room temperature for 18 hours, or an excess of sodium borohydride in methanol at room temperature for 6 hours.

It will be apparent to those skilled in the art that instead of an aldehyde, a ketone or other suitable carbonyl-containing reagent could be used under suitable conditions in the reductive amination step.

(b)—Amide Formation

The formation of a peptide linkage between the acid or acid halide and the amine (VII) may be undertaken by using either:

(i) the acyl halide and the amine (VII), with an excess of acid acceptor in a suitable solvent, or (ii) the acid, optionally with a conventional coupling agent, and the amine (VII), optionally in the presence of a catalyst, with an excess of acid acceptor in a suitable solvent.

Examples of such reaction are as follows:

(i) An acid chloride (optionally generated in-situ) is reacted with an excess of the amine (VII), optionally with an excess of 3° amine such as $Et_3N$, Hünig's base or NMM, in DCM, toluene or dioxane, optionally at elevated temperature for 1 to 24 hrs;

(ii) An acid, WSCDI/DCCI/TBTU and HOBT/HOAT is reacted with an excess of amine (VII) and an excess of NMM, $Et_3N$, Hünig's base in THF, DCM or EtOAc, at rt. for 4 to 48 hrs; or (iii) An acid and PYBOP®/PyBrOP®/Mukaiyama's reagent is reacted with an excess of amine(VII) and an excess of NMM, $Et_3N$, Hünig's base in THF, toluene, DCM or EtOAc, at rt. for 4 to 24 hrs.

Where the acid halide is an acid chloride (i.e. X=Cl), this may be generated in-situ by standard methodology and then reacted with the amine (VII) and triethylamine in dichloromethane at 70° C. for 90 minutes.

(c)—Deprotection

Where PG is a suitable amine-protecting group, preferably BOC, trifluoroacetate or benzyl, the removal of PG from (VIII), to form the unprotected amine (V), is performed by a method selective to the protecting group as detailed in "Protective Groups in Organic Synthesis", $3^{rd}$ edition, by T W Greene and P G M Wuts. John Wiley and Sons, Inc., 1999, incorporated herein by reference.

Examples of such deprotection reactions are as follows:

When PG is BOC, the deprotection involves treatment of (VIII) with an excess of strong acid (e.g. HCl, TFA) at room temperature in a suitable solvent (e.g. DCM, EtOAc, dioxan).

When PG is trifluoroacetate, the deprotection involves treatment of (VIII) with a base (e.g. $K_2CO_3$, $Na_2CO_3$, $NH_3$, $Ba(OH)_2$) in an alcoholic solvent (e.g. MeOH, EtOH), optionally with water and optionally at elevated temperature.

When PG is Bz, the deprotection involves either transfer hydrogenation with a transition metal or transition metal salt hydrogenation catalyst (e.g. Pd/C, $Pd(OH)_2$) in the presence of a hydrogen donor (e.g. $NH_4^+HCO_2^-$) in a polar solvent (e.g. tetrahydrofuran, ethanol, methanol) optionally at elevated temperature and/or pressure, or catalytic hydrogenation in the presence of a palladium or nickel catalyst (e.g. Pd/C, Raney® Ni) under an atmosphere of $H_2$, optionally at elevated temperature and pressure, in a suitable solvent.

More Specifically:

When PG is BOC, the deprotection involves treatment with either an excess of 4M hydrochloric acid in dioxan for 18 hours at room temperature or with TFA in DCM for 4.5 hours at RT.

When PG is trifluoroacetate, the deprotection involves treatment with $K_2CO_3$ in methanol:water mixture (5:1 to 10:1) at room temperature for 18 hours.

When PG is Bz, the deprotection involves treatment with $NH_4^+HCO_2^-$ and 10% Pd/C in ethanol under gentle reflux for between 6 and 20 hours.

Alternative methods for preparing the secondary amine compound (VII) from the primary amine compound (VI) are described in Schemes 1a and 1b below.

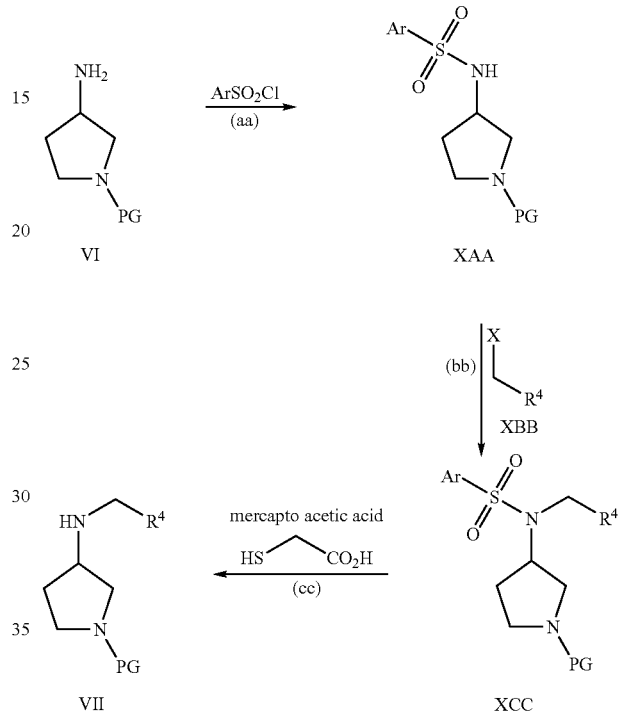

Scheme 1a

Wherein PG is a suitable protecting group and $R^4$ is as defined above.

According to scheme 1a, compounds of formula VII can be prepared from compounds of formula VI by reaction with a sulfonyl chloride, followed by alkylation of the resulting sulfonyl amide, and then removal of the sulfonyl moiety.

(aa) Preparation of the sulfonyl amide. Reaction of equimolar amounts of the primary amine (VI) and a sulfonyl chloride such as 2,4-dinotrobenzenesulphonyl chloride in a suitable solvent (such as DCM, THF or Toluene) in the presence of an organic base (such as pyridine or 2,6-lutidine) or an inorganic base (such as a carbonate salt) for up to 24 hours affords the sulfonylamide (XAA).

(bb) Alkylation of Sulfonviamide XAA. The sulfonylamide of formula XAA is alkylated using an activated alkylating agent XBB, where X is a leaving group such as halogen (such as a iodo, a bromo or a chloro) or a sulfonyl ester (such as a mesylate) in the presence of an organic or an inorganic base, in a suitable solvent (such as DMF or THF). Alternatively the alkylation of sulfonylamide of formula XAA can be achieved using an alcohol XBB (where X is OH), a phosphane (such as triphenyl phosphane) and an azodicarboxylate compound (such as DIAD) in a suitable solvent, such as THF, for up to 24 hours at a temperature between −20 C and 45 C.

(cc) Removal of the sulfonyl group. A compound of formula XCC is treated with an organic base (such as triethyl amine) or an inorganic base (such as a carbonate or a hydroxide) in a suitable solvent (such as DCM, THF or a lower alcohol) and with a thiol (such as mercaptoacetic acid) for up to 24 hours, optionally at an elevated temperature.

Scheme 1b

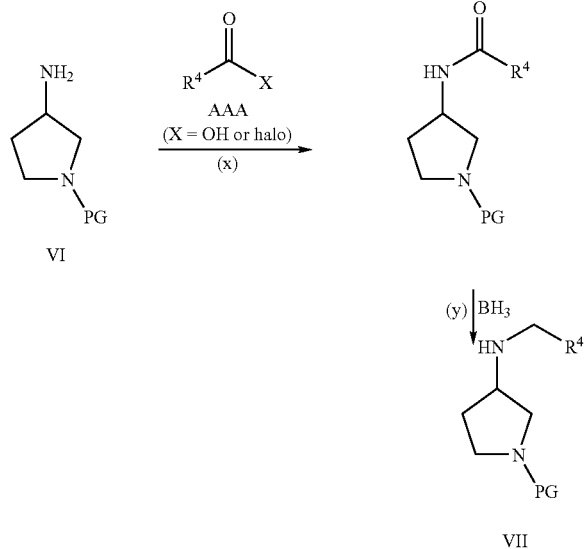

In the above scheme, R⁴ is as defined above and PG is a protecting group.

Acylation-Reduction

According to Scheme 1b, compounds of Formula (VII) may be prepared from 1° amine of Formula (VI) by reaction with a carboxylic acid or acid halide AAA (optionally prepared in-situ) R⁴COX (where X is OH or halo), followed by reaction with a reducing agent, such as borane.

(x)—Amide Formation

The formation of a peptide linkage between the acid or acid halide and the 1° amine (VI) may be undertaken by using either:

(i) the acyl halide and the amine (VI), with an excess of acid acceptor in a suitable solvent, or (ii) the acid, optionally with a conventional coupling agent, and the amine (VI), optionally in the presence of a catalyst, with an excess of acid acceptor in a suitable solvent.

Examples of such reaction are as follows:

(iv) An acid chloride (optionally generated in-situ) is reacted with an excess of the amine (VI), optionally with an excess of 3° amine such as Et₃N, Hünig's base or NMM, in DCM or dioxane, optionally at elevated temperature for 1 to 24 hrs;

(v) An acid, WSCDI/DCCI/TBTU and HOBT/HOAT is reacted with an excess of amine (VI) and an excess of NMM, Et₃N, Hünig's base in THF, DCM or EtOAc, at rt. for 4 to 48 hrs; or (vi) An acid and 1-propyl phosphonic ester cyclic anhydride/PYBOP®/PyBrOP®/Mukaiyama's reagent is reacted with an excess of amine (VI) and an excess of NMM, Et₃N, Hünig's base in THF, DCM or EtOAc, at rt. for 4 to 24 hrs.

A more specific example of the amide formation involves treatment of the acid with the amine in the presence of 1-propyl phosphonic ester cyclic anhydride and in the presence of triethylamine in DCM at room temperature for 1 hour.

Where the acid halide is an acid chloride (i.e. X=Cl), this may be generated in-situ by standard methodology and then reacted with the amine (VI) and triethylamine in dichloromethane at 70° C. for 90 minutes (y)—Reduction The reaction (y) is a reduction of the amide for example by a hydride reducing agent under suitable conditions.

Conveniently, the reduction of the amide is carried out in the presence of Borane in THF at reflux for 2 hours, followed by addition of methanol and aqueous ammonium chloride at reflux for 4 hours.

According to Scheme 2, compounds of Formula (IX) may be prepared from compounds of Formula (VI) by reaction with R⁴—(CH₂)ₐ-L, where a is as defined above and L is a leaving group, under suitable conditions. The resulting compound of Formula (IX) may then be converted to a compound of Formula (I) by amide formation and deprotection in a manner analogous to that described above in relation to Scheme 1.

Scheme 2

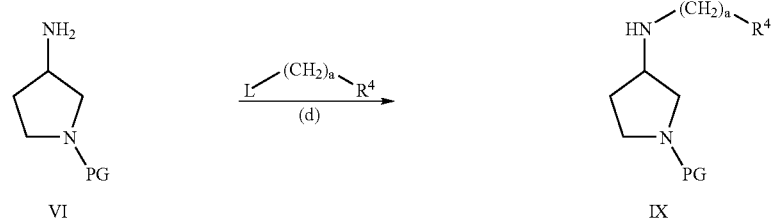

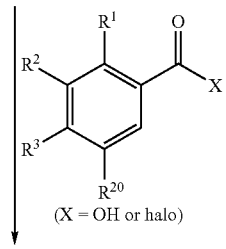

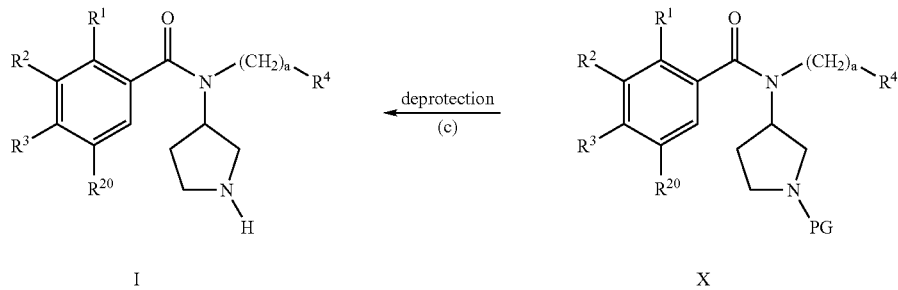

In the above scheme, $R^1$, $R^2$, $R^3$, $R^4$, $R^{20}$ and a are as defined above, PG is a suitable protecting group and L is a leaving group, whose meaning will depend, inter alia, on the nature of the reaction and the specific reaction conditions employed. Suitable leaving groups will be readily apparent to the skilled person and are described in many standard organic chemistry texts, for example: "Advanced Organic Chemistry", Jerry March, Third Edition, Wiley (1985), page 587, incorporated herein by reference; they include halogen (e.g. Br) and sulfonate esters (e.g. methanesulfonate or trifluoromethanesulfonate).

According to Scheme 3, compounds of Formula (IX) may be prepared from a ketone of Formula (XII) by reaction with a primary amine $R^4$—$(CH_2)_a$—$NH_2$ under suitable conditions. The resulting compound of Formula (IX) may then be converted to a compound of Formula (I) by amide formation and deprotection in a manner analogous to that described above in relation to Scheme 1.

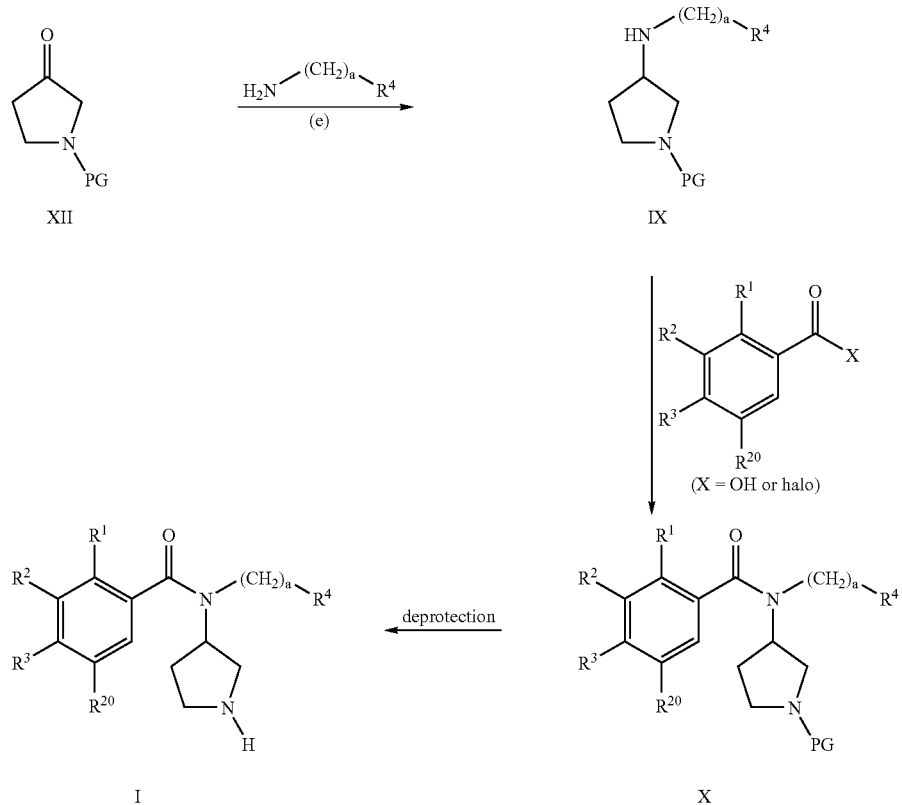

In the above scheme, $R^1$, $R^2$, $R^3$, $R^4$, $R^{20}$ and a are as defined above and PG is a suitable protecting group.

The reaction (e) of the primary amine $R^4$—$(CH_2)_a$—$NH_2$ with the ketone (XII) may conveniently be a reductive amination reaction in which the dehydration of the amine and the ketone is followed by reduction of the resultant imine, for example by a metal hydride reagent or hydrogenation, under suitable conditions.

Conveniently, the reaction of the amine and the ketone is carried out in the presence of titanium (IV) tetraisopropoxide in THF at room temperature for 18 hours, followed by reduction by an excess of sodium borohydride in methanol at room temperature for 5 hours.

The skilled person is able to select the most appropriate synthetic route to the desired compound according to Formula (I). The above schemes may of course be modified as appropriate in accordance with the common general knowledge of those skilled in the art.

It will be appreciated by those skilled in the art that one or more sensitive functional groups may need to be protected and deprotected during the synthesis of a compound of Formula (I). This may be achieved by conventional techniques, for example as described in "Protective Groups in Organic Synthesis", 3$^{rd}$ edition, by T W Greene and P G M Wuts. John Wiley and Sons, Inc., 1999, incorporated herein by reference, which also describes methods for the removal of such groups.

It will be apparent to those skilled in the art that certain protected derivatives of compounds of the invention, which may be made prior to a final deprotection stage, may not possess pharmacological activity as such, but may, in certain instances, be administered orally or parenterally and thereafter metabolized in the body to form compounds of the invention which are pharmacologically active. Such derivatives may therefore be described as prodrugs. Further, certain compounds of the invention may act as prodrugs of other compounds of the invention.

Thus, according to a further aspect of the invention, there is provided a process for preparing compounds of Formula (I), which comprises reacting a compound of formula (IX):

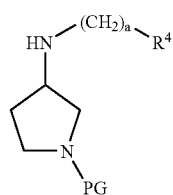

IX wherein R$^4$ and a are as defined above and PG is a protecting group, with an acid or acyl halide of Formula (II):

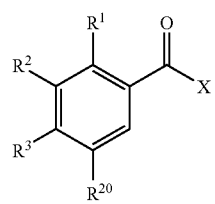

II wherein X is OH or halo, and deprotecting.

Where a is 1, the compound of Formula (IX) may be prepared by reacting a compound of Formula (VI) with an aldehyde R$^4$CHO.

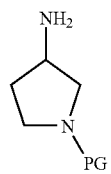

VI

Alternatively, the compound of Formula (IX) may be prepared by reacting a compound of Formula (VI) with a compound R$^4$—(CH$_2$)$_a$-L, where L is a leaving group, optionally selected from halide, methanesulfonate and trifluoromethanesulfonate.

Furthermore, the compound of Formula (IX) may be prepared by reacting a compound of Formula (XII) with a compound R$^4$—(CH$_2$)$_a$—NH$_2$.

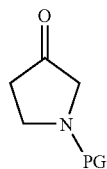

XII

Certain intermediates described above are novel compounds and it is to be understood that all novel intermediates herein for further aspects of the present invention.

Racemic compounds may be separated either using preparative HPLC and a column with a chiral stationary phase, or resolved to yield individual enantiomers utilizing methods known to those skilled in the art. In addition, chiral intermediate compounds may be resolved and used to prepare chiral compounds of the invention.

According to a further aspect of the invention, there is provided one or more metabolites of the compounds of the invention when formed in vivo.

The compounds of the invention may have the advantage that they are more potent, have a longer duration of action, have a broader range of activity, are more stable, have fewer side effects, are more selective, have better tabletting properties, or have other more useful properties than the compounds of the prior art.

The compounds of the invention are useful because they have pharmacological activity in mammals, including humans. Thus, they are useful in the treatment or prevention of disorders in which the regulation of monoamine transporter function is implicated, more particularly disorders in which inhibition of re-uptake of serotonin or noradrenaline is implicated, and especially those in which inhibition of serotonin and noradrenaline re-uptake is implicated.

Accordingly the compounds of the invention are useful in the treatment of urinary incontinence, such as genuine stress incontinence (GSI), stress urinary incontinence (SUI) or urinary incontinence in the elderly; overactive bladder (OAB), including idiopathic detrusor instability, detrusor overactivity secondary to neurological diseases (e.g. Parkinson's disease, multiple sclerosis, spinal cord injury and stroke) and detrusor overactivity secondary to bladder outflow obstruction (e.g. benign prostatic hyperplasia (BPH), urethral stricture or stenosis); nocturnal eneuresis; urinary incontinence due to a combination of the above conditions (e.g. stress incontinence associated with overactive bladder); and lower urinary tract symptoms, such as frequency and urgency. The term OAB is intended to encompass both OAB wet and OAB dry.

In view of their aforementioned pharmacological activity the compounds of the invention are also useful in the treatment of depression, such as major depression, recurrent depression, single episode depression, subsyndromal symptomatic depression, depression in cancer patients, depression in Parkinson's patients, postmyocardial infarction depression, paediatric depression, child abuse induced depression, depression in infertile women, post partum depression, premenstrual dysphoria and grumpy old man syndrome.

In view of their aforementioned pharmacological activity the compounds of the invention are also useful in the treatment of cognitive disorders such as dementia, particularly degenerative dementia (including senile dementia, Alzheimer's disease, Pick's disease, Huntingdon's chorea, Parkinson's disease and Creutzfeldt-Jakob disease) and vascular dementia (including multi-infarct dementia), as well as dementia associated with intracranial space occupying lesions, trauma, infections and related conditions (including HIV infection), metabolism, toxins, anoxia and vitamin deficiency; mild cognitive impairment associated with ageing, particularly age associated memory impairment (AAMI), amnestic disorder and age-related cognitive decline (ARCD); psychotic disorders, such as schizophrenia and mania; anxiety disorders, such as generalised anxiety disorder, phobias (e.g. agoraphobia, social phobia and simple phobias), panic disorder, obsessive compulsive disorder, post traumatic stress disorder, mixed anxiety and depression; personality disorders such as avoidant personality disorder and attention deficit hyperactivity disorder (ADHD); sexual dysfunction, such as premature ejaculation, male erectile dysfunction (MED) and female sexual dysfunction (FSD) (e.g. female sexual arousal disorder (FSAD)); premenstrual syndrome; seasonal affective disorder (SAD); eating disorders, such as anorexia nervosa and bulimia nervosa; obesity; appetite suppression; chemical dependencies resulting from addiction to drugs or substances of abuse, such as addictions to nicotine, alcohol, cocaine, heroin, phenobarbital and benzodiazepines; withdrawal syndromes, such as those that may arise from the aforementioed chemical dependencies; cephalic pain, such as migraine, cluster headache, chronic paroxysmal hemicrania, headache associated with vascular disorders, headache associated with chemical dependencies or withdrawal syndromes resulting from chemical dependencies, and tension headache; pain; Parkinson's diseases, such as dementia in Parkinson's disease, neuroleptic-induced Parkinsonism and tardive dyskinesias); endocrine disorders, such as hyperprolactinaemia; vasospasm, such as in the cerebral vasculature; cerebellar ataxia; Tourette's syndrome; trichotillomania; kleptomania; emotional lability; pathological crying; sleeping disorder (cataplexy); and shock.

From the above conditions, ADHD is of particular interest. The diagnosis of ADHD is based on clinical evaluation (M. Dulcan, et al. *J Am Acad Child Adolesc Psychiatry*, October 1997, 36(10 Suppl), 85S–121S; *National Institutes of Health*, 1998). "The essential feature of ADHD is a persistent pattern of inattention and/or hyperactivity-impulsivity that is more frequent and severe than is typically observed in individuals at a comparative level of development" (Diagnostic and Statistical Manual of Mental Disorders (DSM-IV), American Psychiatric Association, Washington, D.C., 1994). In order to be diagnosed with ADHD, patients must demonstrate symptoms of ADHD that cause impairment before the age of seven years, and symptoms must have been ongoing for longer than six months in at least two settings (e.g., school [or work] and home). (See DSM-IV).

In view of their aforementioned pharmacological activity the compounds of the invention are also useful in the treatment of a number of other conditions or disorders, including hypotension; gastrointestinal tract disorders (involving changes in motility and secretion) such as irritable bowel syndrome (IBS), ileus (e.g. post-operative ileus and ileus during sepsis), gastroparesis (e.g. diabetic gastroparesis), peptic ulcer, gastroesophageal reflux disease (GORD, or its synonym GERD), flatulence and other functional bowel disorders, such as dyspepsia (e.g. non-ulcerative dyspepsia (NUD)) and non-cardiac chest pain (NCCP); and fibromyalgia syndrome.

The compounds of the invention, being serotonin and/or noradrenaline reuptake inhibitors are potentially useful in the treatment of a range of disorders, including pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1–164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually in twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765–1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13–44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13–44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), posttraumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959–1964). The symptoms of neuropathic pain are difficult to treat, as they are often heterogeneous even between patients with the same disease (Woolf & Decosterd, 1999, Pain Supp., 6, S141–S147; Woolf and Mannion, 1999, Lancet, 353, 1959–1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45–56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397–407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679–686; McCarthy et al., 1994, Textbook of Pain, 387–395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other Types of Pain Include:

pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;

heart and vascular pain, including pain caused by angina, myocardical infarction, mitral stenosis, pericarditis, Raynaud's phenomenon, scleredoma and skeletal muscle ischemia;

head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

Disorders of particular interest include urinary incontinence, such as mixed incontinence, GSI and USI; pain; depression; anxiety disorders, such as obsessive-compulsive disorder and post traumatic stress disorder; personality disorders, such as ADHD; sexual dysfunction; and chemical dependencies and withdrawal syndromes resulting from chemical dependencies.

Thus, According to Further Aspects, the Invention Provides:

i) a compound of the invention for use in human or veterinary medicine;

ii) a compound of the invention for use in the treatment of a disorder in which the regulation of monoamine transporter function is implicated, such as urinary incontinence;
iii) the use of a compound of the invention in the manufacture of a medicament for the treatment of a disorder in which the regulation of monoamine transporter function is implicated;
iv) a compound of the invention for use in the treatment of a disorder in which the regulation of serotonin or noradrenaline is implicated;
v) the use of a compound of the invention in the manufacture of a medicament for the treatment of a disorder in which the regulation of serotonin or noradrenaline is implicated;
vi) a compound of the invention for use in the treatment of a disorder in which the regulation of serotonin and noradrenaline is implicated;
vii) the use of a compound of the invention in the manufacture of a medicament for the treatment of a disorder in which the regulation of serotonin and noradrenaline is implicated;
viii) a compound of the invention for use in the treatment of urinary incontinence, such as GSI or USI;
ix) the use of a compound of the invention in the manufacture of a medicament for the treatment of urinary incontinence, such as GSI or USI;
x) a method of treatment of a disorder in which the regulation of monoamine transporter function is implicated which comprises administering a therapeutically effective amount of a compound of the invention to a patient in need of such treatment;
xi) a method of treatment of a disorder in which the regulation of serotonin or noradrenaline is implicated which comprises administering a therapeutically effective amount of a compound of the invention to a patient in need of such treatment;
xii) a method of treatment of a disorder in which the regulation of serotonin and noradrenaline is implicated which comprises administering a therapeutically effective amount of a compound of the invention to a patient in need of such treatment; and
xiii) a method of treatment of urinary incontinence, such as GSI or USI, which comprises administering a therapeutically effective amount of a compound of the invention to a patient in need of such treatment.

It is to be appreciated that all references herein to treatment include curative, palliative and prophylactic treatment, unless explicitly stated otherwise.

The compounds of the invention may be administered alone or as part of a combination therapy. If a combination of therapeutic agents is administered, then the active ingredients may be administered either sequentially or simultaneously in separate or combined pharmaceutical formulations.

Examples of suitable agents for adjunctive therapy include:
- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an $H_1$ antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;
- an alpha-adrenergic, e.g. doxazosin, tamsulosin, clonidine, guanfacine, dexmetatomidine, modafinil, phentolamine, terazasin, prazasin or 4-amino-6,7-dimethoxy-2-(5-methane-sulfonamido-1,2,3,4-tetrahydroisoquinol-2-yl)-5-(2-pyridyl) quinazoline;
- a tricyclic antidepressant, e.g. desipramine, imipramine, amitriptyline or nortriptyline;
- an anticonvulsant, e.g. carbamazepine, lamotrigine, topiratmate or valproate;
- a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);
- a muscarinic antagonist, e.g oxybutynin, tolterodine, propiverine, tropsium chloride, darifenacin, solifenacin, temiverine and ipratropium;
- a COX-2 selective inhibitor, e.g. celecoxib, rofecoxib, parecoxib, valdecoxib, deracoxib, etoricoxib, or lumiracoxib;
- a coal-tar analgesic, in particular paracetamol;
- a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-HT$_{1B/1D}$ agonist such as eletriptan, sumatriptan, naratriptan, zolmitriptan or rizatriptan;

a 5-HT$_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl -7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E$_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl), 1,4-benzoquinone (CV-6504);

a sodium channel blocker, such as lidocaine;

a 5-HT3 antagonist, such as ondansetron, granisetron, tropisetron, azasetron, dolasetron or alosetron;

an oestrogen agonist or selective oestrogen receptor modulator (e.g. HRT therapies or lasofoxifene);

an alpha-adrenergic receptor agonist, such as phenylpropanolamine or R-450;

a dopamine receptor agonist (e.g. apomorphine, teachings on the use of which as a pharmaceutical may be found in U.S. Pat. No. 5,945,117), including a dopamine D2 receptor agonist (e.g. premiprixal, Pharmacia Upjohn compound number PNU95666; or ropinirole);

a PGE1 agonist (e.g. alprostadil);

and the pharmaceutically acceptable salts and solvates thereof.

The invention thus provides, in a further aspect, a combination comprising a compound of the invention together with a further therapeutic agent.

For human use the compounds of the invention can be administered alone, but in human therapy will generally be administered in admixture with a suitable pharmaceutical excipient, diluent or carrier selected with regard to the intended route of administration and standard pharmaceutical practice.

For example, the compounds of the invention, can be administered orally, buccally or sublingually in the form of tablets, capsules (including soft gel capsules), ovules, elixirs, solutions or suspensions, which may contain flavouring or colouring agents, for immediate-, delayed-, modified-, sustained-, dual-, controlled-release or pulsatile delivery applications. The compounds of the invention may also be administered via intracavernosal injection. The compounds of the invention may also be administered via fast dispersing or fast dissolving dosage forms.

Such tablets may contain excipients such as microcrystalline cellulose, lactose, sodium citrate, calcium carbonate, dibasic calcium phosphate, glycine, and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention, and their pharmaceutically acceptable salts, may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form, i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds of the invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

For oral and parenteral administration to human patients, the daily dosage level of the compounds of the invention or salts or solvates thereof will usually be from 10 to 500 mg (in single or divided doses).

Thus, for example, tablets or capsules of the compounds of the invention or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including PE), compounds of the invention may be taken as a single dose on an "as required" basis (i.e. as needed or desired).

Example Tablet Formulation

In general a tablet formulation could typically contain between about 0.01 mg and 500 mg of a compound according to the present invention (or a salt thereof) whilst tablet fill weights may range from 50 mg to 1000 mg. An example formulation for a 10 mg tablet is illustrated:

| Ingredient | % w/w |
|---|---|
| Free base or salt of compound | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity and is based on the weight of the free base.

The compounds of the invention can also be administered intranasally or by inhalation and are conveniently delivered in the form of a dry powder inhaler or an aerosol spray presentation from a pressurised container, pump, spray or nebulizer with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

The compounds of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds of the invention can be administered in the form of a suppository or pessary, or they may be applied topically in the form of a gel, hydrogel, lotion, solution, cream, ointment or dusting powder. The compounds of the invention may also be dermally or transdermally administered, for example, by the use of a skin patch. They may also be administered by the ocular, pulmonary or rectal routes.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters, wax, cetearyl alcohol, 2-octyidodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

For oral or parenteral administration to human patients the daily dosage levels of compounds of formula (I), and their pharmaceutically acceptable salts, will be from 0.01 to 30 mg/kg (in single or divided doses) and preferably will be in the range 0.01 to 5 mg/kg. Thus tablets will contain 1 mg to 0.4 g of compound for administration singly or two or more at a time, as appropriate. The physician will in any event determine the actual dosage which will be most suitable for any particular patient and it will vary with the age, weight and response of the particular patient. The above dosages are, of course only exemplary of the average case and there may be instances where higher or lower doses are merited, and such are within the scope of the invention.

Oral Administration is Preferred.

For veterinary use, a compound of the invention is administered as a suitably acceptable formulation in accordance with normal veterinary practice and the veterinary surgeon will determine the dosing regimen and route of administration which will be most appropriate for a particular animal.

Thus according to a further aspect, the invention provides a pharmaceutical formulation containing a compound of the invention and a pharmaceutically acceptable adjuvant, diluent or carrier.

The combinations referred to above may also conveniently be presented for use in the form of a pharmaceutical formulation and thus pharmaceutical formulations comprising a combination as defined above together with a pharmaceutically acceptable adjuvant, diluent or carrier comprise a further aspect of the invention. The individual components of such combinations may be administered either sequentially or simultaneously in separate or combined pharmaceutical formulations.

When a compound of the invention is used in combination with a second therapeutic the dose of each compound may differ from that when the compound is used alone. Appropriate doses will be readily appreciated by those skilled in the art.

The invention is illustrated by the following non-limiting examples in which the following abbreviations and definitions may be used:

| | |
|---|---|
| APCI | Atmospheric pressure chemical ionisation |
| Arbacel ® | filter agent |
| br | Broad |
| BOC | tert-butoxycarbonyl |
| CDI | carbonyldiimidazole |
| ☐ | chemical shift |
| d | doublet |
| ☐ | heat |
| DCCI | dicyclohexylcarbodiimide |
| DCM | dichloromethane |
| DMF | N,N-dimethylformamide |
| DMSO | dimethylsulfoxide |
| ES$^+$ | electrospray ionisation positive scan |
| ES$^-$ | electrospray ionisation negative scan |
| h | hours |
| HOAT | 1-hydroxy-7-azabenzotriazole |
| HOBT | 1-hydroxybenzotriazole |
| HPLC | high pressure liquid chromatography |
| m/z | mass spectrum peak |
| min | minutes |
| MS | mass spectrum |
| NMM | N-methyl morpholine |
| NMR | nuclear magnetic resonance |
| q | quartet |
| s | singlet |
| t | triplet |
| TBTU | 2-(1H-benzotriazol-1-yl)-1,1,3,3-tetramethyluronium tetrafluoroborate |
| Tf | trifluoromethanesulfonyl |
| TFA | trifluoroacetic acid |
| THF | tetrahydrofuran |
| TLC | thin layer chromatography |
| TS$^+$ | thermospray ionisation positive scan |
| WSCDI | 1-(3-dimethylaminopropyl)-3-ethylcarbodiimide hydrochloride |

The Preparations and Examples that follow illustrate the invention but do not limit the invention in any way.

All temperatures are in ° C. Flash column chromatography was carried out using Merck silica gel 60 (9385). Solid Phase Extraction (SPE) chromatography was carried out using Varian Mega Bond Elut (Si) cartridges (Anachem) under 15 mmHg vacuum. Thin layer chromatography (TLC) was carried out on Merck silica gel 60 plates (5729). Melting points were determined using a Gallenkamp MPD350 apparatus and are uncorrected. NMR was carried out using a Varian-Unity Inova 400 MHz nmr spectrometer or a Varian Mercury 400 MHz nmr spectrometer. Mass spectroscopy was carried out using a Finnigan Navigator single quadrupole electrospray mass spectrometer or a Finnigan aQa APCI mass spectrometer.

Conveniently, compounds of the invention are isolated following work-up in the form of the free base, but pharmaceutically acceptable acid addition salts of the compounds of the invention may be prepared using conventional means. Solvates (e.g. hydrates) of a compound of the invention may be formed during the work-up procedure of one of the aforementioned process steps.

Where compounds were prepared in the manner described for an earlier Example, the skilled person will appreciate that reaction times, number of equivalents of reagents and reaction temperatures may be modified for each specific reaction, and that it may nevertheless be necessary or desirable to employ different work-up or purification conditions.

Preparation 1 tert-butyl (3S)-3-(cyclopentylamino)pyrrolidine-1-carboxylate

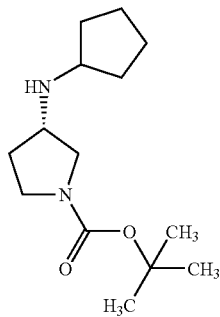

Cyclopentanone (12.7 ml, 143 mmol) was added to tert-butyl (3S)-3-aminopyrrolidine-1-carboxylate (26.6 g, 143 mmol) in a mixture methanol:toluene 3:1 (600 ml:200 ml) and the reaction mixture was stirred at room temperature for 1.5 hours under nitrogen. The mixture was then evaporated to 50 ml, azeotroped three times with methanol:toluene 3:1 (600 ml:200 ml) and concentrated in vacuo. The reaction mixture was taken up in methanol (250 ml), cooled down to 0° C. and sodium borohydride (7.5 g, 200.2 mmol) was added portionwise. After completion of the reaction, water (50 ml) was added and the solvent was evaporated. The residue was diluted with more water (150 ml) and extracted three times with dichloromethane (250 ml). The organic phases were combined, dried over magnesium sulfate, and concentrated in vacuo to provide the title compound as a gum, 36.1 g (99.4%).

$^1$HNMR(CDCl$_3$, 400 MHz)δ: 1.18(brs, 1H), 1.28(m, 2H), 1.44(s, 9H), 1.52(m, 2H), 1.67(m, 3H), 1.83(m, 2H), 2.05(m, 1H), 2.98(m, 1H), 3.08(m, 1H), 3.30(m, 2H), 3.45(m, 1H), 3.58(m, 1H) MS APCI$^+$ m/z 255 [MH]$^+$ Preparation 2 tert-Butyl (3S)-3-[cyclopentyl(2,3-dichlorobenzoyl)amino]pyrrolidine-1-carboxylate

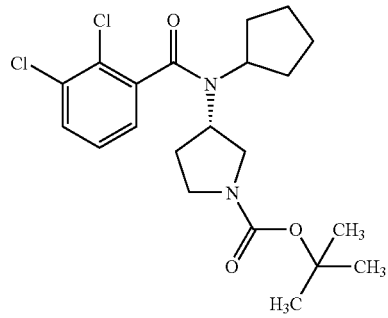

Triethylamine (24 ml, 170 mmol) was added to a solution of the amine of preparation 1 (36.1 g, 142 mmol) in dichloromethane (350 ml) under nitrogen. The reaction mixture was cooled to 0° C. and 2,3-dichloro-benzoyl chloride (29.8 g, 142 mmol) in dichloromethane was added dropwise keeping the temperature below 5° C. The reaction mixture was then stirred for 6 hours. Water (200 ml) was added and the organic phase collected. The aqueous layer was extracted with dichloromethane (250 ml). The combined organic phases were washed with 2M aqueous sodium hydroxide and 10% citric acid solution, dried over magnesium sulfate and concentrated in vacuo. The crude product was purified by column chromatography on silica gel eluting with ethyl acetate:cyclohexane (1:6 to 1:4 to 1:2 to 1:1 by volume) to yield the title product, 50 g (82.4%).

$^1$HNMR(CDCl$_3$, 400 MHz, rotamers) δ: 1.43–1.47(d, 9H), 1.56–1.66(m, 5H), 1.79(m, 0.5H), 1.98(m, 3H), 2.37 (m, 1H), 2.92(m, 0.5H), 3.15(m, 0.5H), 3.40(m, 1H), 3.58 (m, 1.5H), 3.74(m, 2H), 3.97(m, 1H), 7.10(m, 1H), 7.24(m, 1H), 7.46(d, 1H) MS APCI$^+$ m/z 427 [MH]$^+$ and m/z 327[MH-Boc]$^+$ Preparation 3 tert-Butyl (3S)-3-[cyclopentyl(2,3-dichloro-4-fluorobenzoyl)amino]pyrrolidine-1-carboxylate

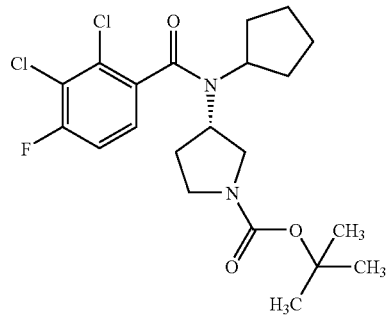

Oxalyl chloride (2.13 ml, 24.4 mmol) was added to a suspension of 2,3-dichloro-4-fluoro benzoic acid (4.25 g, 20.33 mmol) (see EP0600317, example 15) in dry dichloromethane (41 ml) at room temperature under nitrogen. N,N-dimethylformamide (80 □l, 1 mmol) was added and the reaction mixture stirred for 1 hour. Solvent was removed by evaporation under reduced pressure to produce a yellow solid, which was dissolved in dichloromethane (20 ml) and added dropwise to solution of triethylamine (4.72 ml, 33.9 mmol) and the amine of preparation 1 (4.31 g, 16.95 mmol) in dichloromethane (36 ml) under nitrogen. After stirring for 18 hours at room temperature, the resultant mixture was diluted with dichloromethane (100 ml) and 1M aqueous potassium carbonate (90 ml). The organic phase was dried over magnesium sulfate, filtered and the solvent was removed by evaporation under reduced pressure. The residue was dissolved in minimum quantity of dichloromethane and purified by chromatography on silica gel eluting with a solvent gradient of pentane changing to ethyl acetate: pentane (20:80, by volume) to produce the title compound as a white foam, 6.6 (73%).

$^1$HNMR(CD$_3$OD, 400 MHz, rotamers) δ: 1.43–1.47(d, 9H), 1.62(m, 1.5H), 1.72(m, 3H), 1.88(m, 1.5H), 1.97(m, 0.5H), 2.13(m, 1.5H), 2.32(m, 0.5H), 2.74(m, 1H), 3.40(m, 1H), 3.51–3.59(m, 1.5H), 3.76(m, 2H), 3.88(m, 1H), 4.05 (m, 1H), 7.33(m, 2H)

Preparation 4 tert-Butyl (3S)-3-(cyclohexylamino)pyrrolidine-1-carboxylate

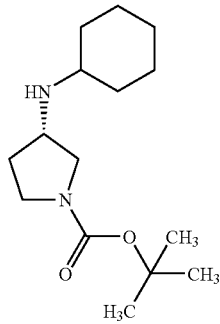

tert-butyl (3S)-3-(cyclohexylamino)pyrrolidine-1-carboxylate was prepared by a method similar to that described in preparation 1 using tert-butyl (3S)-3-aminopyrrolidine-1-carboxylate and cyclohexanone to yield the desired product, 5.9 g (82%).

$^1$HNMR(CDCl$_3$, 400 MHz) δ: 1.09(m, 2H), 1.24(m, 3H), 1.45(s, 9H), 1.62(m, 2H), 1.72(m, 2H), 1.88(m, 2H), 2.06(m, 1H), 2.48(m, 1H), 3.01(m, 1H), 3.30(m, 1H), 3.45(m, 2H), 3.55–3.62(m, 1H) MS APCI$^+$ m/z 269 [MH]$^+$

Preparation 5 tert-Butyl (3S)-3-[cyclohexyl(2,3-dichloro-benzoyl)amino]pyrrolidine-1-carboxylate

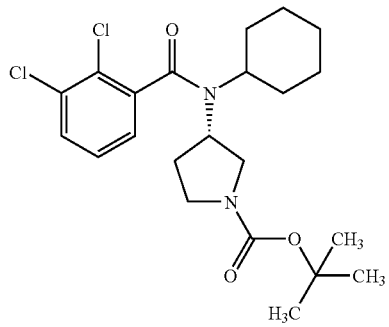

tert-Butyl-(3S)-3-[cyclohexyl(2,3-dichlorobenzoyl)amino]pyrrolidine-1-carboxylate was prepared by a method similar to that described in preparation 2 using the amine of preparation 4 and 2,3-dichlorobenzoyl chloride to yield the desired product, 5.14 g (83%).

$^1$HNMR(CDCl$_3$, 400 MHz, rotamers) δ: 1.00–1.09(m, 2H), 1.26(m, 1H), 1.43–1.47(d, 9H), 1.58(m, 3H), 1.73(m, 2H), 1.89(m, 2H), 2.68(m, 1H), 2.89(m, 1H), 3.10(m, 1H), 3.39(m, 1H), 3.52(m, 1H), 3.69(m, 1H), 3.92(m, 2H), 7.10 (m, 1H), 7.23(m, 1H), 7.47(d, 1H) LCMS ELSD/APCI$^+$ m/z 441 [MH]$^+$ Preparation 6 tert-Butyl (3S)-3-[cyclohexyl(2-chloro-3-fluorobenzoyl)amino]pyrrolidine-1-carboxylate

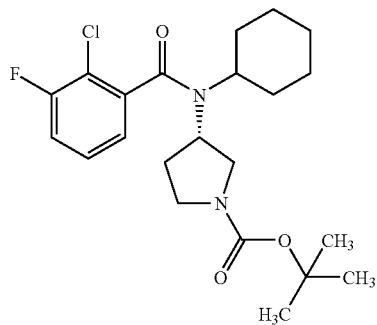

tert-Butyl(3S)-3-[cyclohexyl(2-chloro-3-fluorobenzoyl) amino]pyrrolidine-1-carboxylate was prepared by a method similar to that described in preparation 3 using the amine of preparation 4 and 2-chloro-3-fluoro benzoic acid to yield the desired product, 158 mg (29%).

$^1$HNMR(CDCl$_3$, 400 MHz, rotamers) δ: 0.98–1.06(m, 2.5H), 1.29(m, 1.5H), 1.47(d, 9H), 1.57(m, 3H), 1.73(m, 2H), 1.87(m, 2H), 2.66(m, 0.5H), 2.89(m, 1H), 3.11(m, 1H), 3.38(m, 1H), 3.53(m, 1H), 3.69(m, 0.5H), 3.91(m, 2H), 6.99(m, 1H), 7.15(t, 1H), 7.28(m, 1H) MS APCI$^+$ m/z 425 [MH]$^+$ and m/z 325[MH-Boc]$^+$ Preparation 7 tert-Butyl (3S)-3-[cyclohexyl(3-fluoro-2-methylbenzoyl)amino]pyrrolidine-1-carboxylate

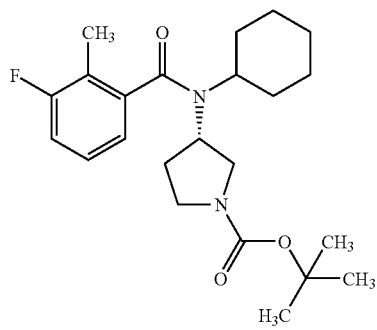

tert-Butyl(3S)-3-[cyclohexyl(3-fluoro-2-methylbenzoyl) amino]pyrrolidine-1-carboxylate was prepared by a method similar to that described in preparation 3 using the amine of preparation 4 and 3-fluoro-2-methyl benzoic acid to yield the desired product, 63 mg (12%).

$^1$HNMR(CDCl$_3$, 400 MHz, rotamers) δ: 1.02(m, 2.5H), 1.30(m, 2.5H), 1.47(d, 9H), 1.57(m, 1H), 1.62(m, 4H), 1.73(m, 1H), 1.91(m, 1H), 2.20(s, 3H), 2.71(m, 0.5H), 2.91(m, 1H), 3.18(m, 1H), 3.39(m, 1H), 3.49(m, 0.5H), 3.68(m, 0.5H), 3.85–3.93(m, 1.5H), 6.87(d, 1H), 7.01(t, 1H), 7.17(q, 1H) MS APCI$^+$ m/z 405 [MH]$^+$ and m/z 305[MH-Boc]$^+$ Preparation 8 tert-butyl (3S)-3-(cyclobutylamino)pyrrolidine-1-carboxylate

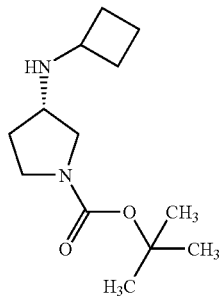

tert-butyl (3S)-3-(cyclobutylamino)pyrrolidine-1-carboxylate was prepared by a method similar to that described in preparation 1 using tert-butyl (3S)-3-aminopyrrolidine-1-carboxylate and cyclobutanone (15 equivalents: 10 eq. added first, 5 eq. added before the second azeotropic removal of water) except that the crude product was purified by column chromatography on silica gel to yield the title compound, 542 mg (28%).

$^1$HNMR(CD$_3$OD, 400 MHz) δ: 1.45(s, 9H), 1.70(m, 3H), 1.81(m, 3H), 2.05(m, 1H), 2.21(m, 2H), 3.03(m, 1H), 3.26(m, 2H), 3.47(m, 2H) MS APCI$^+$ m/z 241 [MH]$^+$

Preparation 9 tert-Butyl (3S)-3-[cyclobutyl(2,3-dichloro-benzoyl)amino]pyrrolidine-1-carboxylate

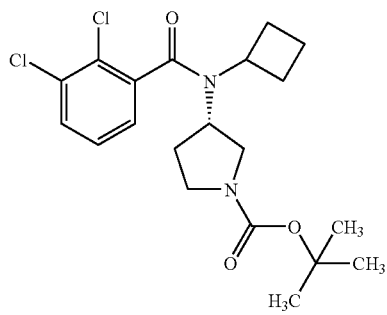

tert-Butyl-(3S)-3-[cyclobutyl(2,3-dichlorobenzoyl)amino] pyrrolidine-1-carboxylate was prepared by a method similar to that described in preparation 2 using the amine of preparation 8 and 2,3-dichlorobenzoyl chloride to yield the desired product, 370 mg (79%).

$^1$HNMR(CD$_3$OD, 400 MHz) δ: 1.43(m, 1H), 1.48(s, 9H), 1.66(m, 1H), 1.95(m, 1H), 2.12–2.27(m, 4H), 2.72(m, 1H), 3.42(m, 1H), 3.61 (m, 1H), 3.69(m, 1H), 3.86(m, 1H), 3.98(m, 1H), 4.45(m, 1H), 7.24(dd, 1H), 7.40(t, 1H), 7.62(d, 1H) MS APCI$^+$ m/z 313 [MH-Boc]$^+$

Preparation 10 tert-butyl (3S)-3-{[(2,4-dinitrophenyl)sulfonyl]amino}pyrrolidine-1-carboxylate

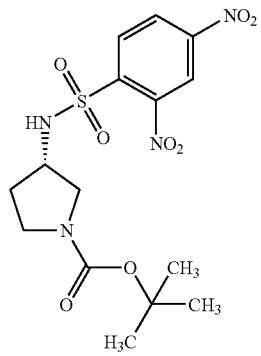

tert-butyl (3S)-3-aminopyrrolidine-1-carboxylate (5 g, 27 mmol) was added to a solution of 2,6-lutidine (6.2 mL, 54 mmol) in dichloromethane (150 ml) under nitrogen. The reaction mixture was cooled down to 0° C. and a solution of 2,4-dinitrobenzenesulphonyl chloride (7.15 g, 27 mmol) in dichloromethane (100 ml) was slowly added over 15 minutes at 0° C. The reaction mixture was then stirred at room temperature for 48 hours under nitrogen. Water (100 ml) was added followed by 2N aqueous hydrogen chloride until the aqueous layer reached pH 2. The layers were then separated and the aqueous layer extracted with more dichloromethane (100 ml). The organic phases were combined, washed twice with water (100 ml), dried over magnesium sulfate and concentrated in vacuo to provide the title compound as a gum, 10 g (89%).

$^1$HNMR(CDCl$_3$, 400 MHz) δ: 1.42(s, 9H), 1.88(m, 1H), 2.15(m, 1H), 3.18(m, 1H), 3.37–3.44(m, 2H), 4.07(m, 1H), 5.58(d, 1H), 8.40(d, 1H), 8.57(d, 1H), 8.68(s, 1H),

Preparation 11 tert-butyl (3S)-3-(cyclobutylmethylamino)pyrrolidine-1-carboxylate

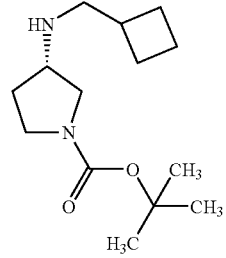

Cyclobutane methanol (0.2 ml, 2.11 mmol) followed by triphenylphosphine (465 mg, 2.3 mmol) were added to a solution of the compound from preparation 10 (0.8 g, 1.92 mmol) in tetrahydrofuran (40 ml) under nitrogen. The reaction mixture was cooled down to 0° C. and a solution of diisopropyl azodicarboxylate (0.45 ml, 2.3 mmol) in tetrahydrofuran (15 ml) was added dropwise with the temperature kept below 3° C. The reaction mixture was stirred at 0° C. for 0.5 hour and then at room temperature for 18 hours. Tetrahydrofuran was evaporated and the residue taken up in dichloromethane (20 ml). Triethylamine (0.53 ml, 3.84 mmol) and mercapto acetic acid (0.16 ml, 2.3 mmol) were added and the reaction mixture was stirred at room temperature for 2 hours. It was then washed with 2N aqueous hydrogen chloride. The aqueous layer was basified to pH11 with 2M sodium hydroxide and back-extracted three times with ethyl acetate. The organic phases were then concentrated in vacuo to provide the title compound (151 mg, 31%).

$^1$HNMR(CDCl$_3$, 400 MHz) δ: 1.44(s, 9H), 1.65(m, 3H), 1.87(m, 2H), 2.05(m, 3H), 2.45(m, 1H), 2.62(d, 1H), 3.05 (m, 1H), 3.28–3.51 (m, 5H)

Alternative Method

Borane tetrahydrofuran complex (1M in tetrahydrofuran, 100 ml, 100 mmol) was added to a solution of the compound from preparation 27 (9 g, 33.54 mmol) in anhydrous tetrahydrofuran (100 ml) under nitrogen. The reaction mixture was refluxed for 2 hours. The reaction mixture was cooled to room temperature, quenched with methanol and concentrated in vacuo. The residue was azeotroped with methanol then re-dissolved in methanol (200 ml), heated under reflux for 18 hours then concentrated in vacuo. Purification of the residue by chromatography on silica gel, eluting with dichloromethane:methanol:0.88 ammonia, (95:5:0.5, by volume) afforded the title compound as a gum, (7.67 g, 90%).

$^1$HNMR(400 MHz, CD$_3$OD) δ: 1.44 (s, 9H), 1.70 (m, 3H), 1.90 (m, 2H), 2.08 (m, 3H), 2.47 (m, 1H), 2.62 (m, 2H), 3.06 (m, 1H), 3.27 (m, 2H), 3.45 (m, 1H), 3.54 (m, 1H) MS APCI m/z 255 [MH]$^+$

Preparation 12 tert-Butyl (3S)-3-[cyclobutylmethyl(2,3-dichlorobenzoyl)amino]pyrrolidine-1-carboxylate

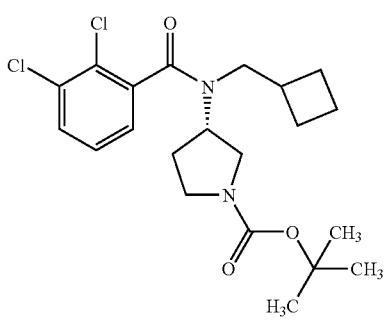

tert-Butyl(3S)-3-[cyclobutylmethyl(2,3-dichlorobenzoyl)amino]pyrrolidine-1-carboxylate was prepared by a method similar to that described in preparation 2 using the amine of preparation 11 and 2,3-dichlorobenzoyl chloride to yield the desired product, 94 mg (37%).

LCMS ELSD/APCI$^+$ m/z 427 [MH]$^+$

Preparation 13 tert-butyl (3S)-3-(cyclopropylmethylamino)pyrrolidine-1-carboxylate

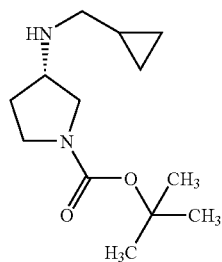

tert-butyl (3S)-3-(cyclopropylmethylamino)pyrrolidine-1-carboxylate was prepared by a method similar to that described in preparation 1 using tert-butyl (3S)-3-aminopyrrolidine-1-carboxylate and cyclopropane carboxaldehyde except that the crude product was purified by chromatography on silica gel eluting with a solvent gradient of dichloromethane changing to dichloromethane:methanol:0.88 ammonia (90:10:1 by volume) to yield the title compound, 5.2 g (81%).

$^1$HNMR(CDCl$_3$, 400 MHz) δ: 0.15(m, 2H), 0.48(m, 2H), 0.97(m, 1H), 1.43(s, 9H), 1.75(m, 1H), 2.05(m, 1H), 2.50(d, 2H), 3.10(m, 1H), 3.47(m, 2H), 3.50(m, 2H) MS APCI$^+$ m/z 241 [MH]$^+$

Preparation 14 tert-butyl (3S)-3-(tetrahydro-2H-pyran-4-ylamino) pyrrolidine-1-carboxylate

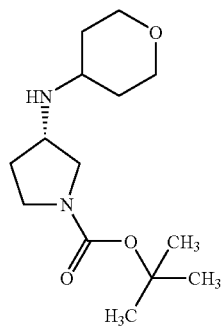

tert-butyl (3S)-3-aminopyrrolidine-1-carboxylate was added to a solution of tetrahydro-4H-pyran-4-one and 10% Pd/C (300 mg) in ethanol and the reaction mixture left under about 415 kPa (about 60 psi) of hydrogen gas for 18 hours. The reaction mixture was filtered through Arbocel®, washing through thoroughly with ethyl acetate. The filtrate was concentrated in vacuo and the crude product purified by column chromatography on silica gel to yield the desired product, 6.7 g (61%).

$^1$HNMR(CDCl$_3$, 400 MHz) δ: 1.39(m, 2H), 1.46(s, 9H), 1.67(m, 1H), 1.82(m, 2H), 2.07(m, 1H), 2.72(m, 1H), 3.02 (brm, 1H), 3.31–3.39(m, 5H), 3.59(brm, 1H), 3.96(m, 2H) MS ES+ m/z 271 [MH]$^+$

Preparation 15 tert-butyl (3S)-3-[(2,3-dichlorobenzoyl)(tetrahydro-2H-pyran-4-yl)amino]pyrrolidine-1-carboxylate

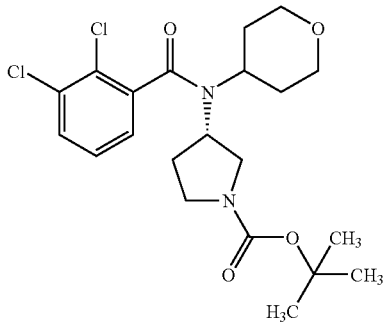

tert-butyl(3S)-3-[(2,3-dichlorobenzoyl)(tetrahydro-2H-pyran-4-yl)amino]pyrrolidine-1-carboxylate was prepared by a method similar to that described in preparation 2 (using N-Methyl Morpholine as base) from the amine of preparation 14 and 2,3-dichlorobenzoyl chloride to yield the desired product, 200 mg (31%).

$^1$HNMR (CD$_3$OD, 400 MHz) δ: 1.43–1.47(d, 9H), 1.58 (m, 1.5H), 1.76(m, 0.5H), 1.94(m, 2H), 2.11(m, 1H), 2.76 (m, 0.5H), 2.98(m, 0.5H), 3.13(m, 2H), 3.4–3.58(m, 4H), 3.69(m, 0.5H), 3.9(m, 2.5H), 4.04(m, 0.5H), 4.2(m, 0.5H), 7.29(d, 1H), 7.43(t, 1H), 7.62(d, 1H) rotamers MS APCI+ m/z 443 [MH]+ and 343 [MH-Boc]+

Preparation 16 tert-Butyl (3S)-3-[(2-chlorobenzoyl)(cyclopentyl)amino]pyrrolidine-1-carboxylate

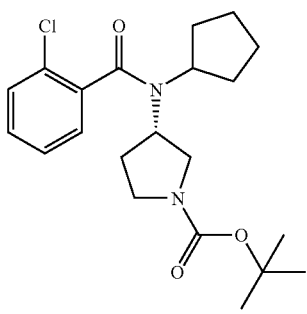

tert-Butyl-(3S)-3-[(2-chlorobenzoyl)(cyclopentyl)amino]pyrrolidine-1-carboxylate was prepared by a method similar to that described in preparation 2 (using Toluene as solvent, N-Methyl Morpholine as base, and heating the reaction mixture at 60° C. for 18 hours) using the amine of preparation 1 and 2-chlorobenzoyl chloride to yield the desired product, 1.16 g (75%).

$^1$HNMR(CD$_3$OD, 400 MHz, rotamers) δ: 1.42–1.47(d, 11H), 1.62(m, 1H), 1.71 (m, 3H), 1.89(m, 1H), 1.99(m, 1H), 2.13(m, 1H), 2.33(m, 0.5H), 2.77(m, 1H), 3.07(m, 0.5H), 3.46(m, 1H), 3.60(m, 0.5H), 3.70(m, 1H), 3.78(m, 1H), 3.90(m, 0.5H), 4.04(m, 1H), 7.30(m, 1H), 7.41(m, 2H), 7.48(m, 1H) MS APCI$^+$ m/z 393 [MH]$^+$ and m/z 293 [MH-Boc]$^+$

Preparation 17 tert-Butyl (3S)-3-[(2-chlorobenzoyl)(cyclohexyl)amino]pyrrolidine-1-carboxylate

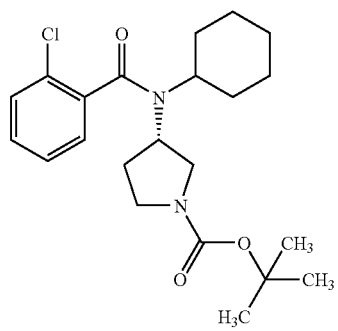

tert-Butyl-(3S)-3-[(2-chlorobenzoyl)(cyclohexyl)amino]pyrrolidine-1-carboxylate was prepared by a method similar to that described in preparation 2 (using Toluene as solvent, N-Methyl Morpholine as base, and heating the reaction mixture at 60° C. for 18 hours) using the amine of preparation 4 and 2-chlorobenzoyl chloride to yield the desired product, 1.09 g (72%).

$^1$HNMR(CD$_3$OD, 400 MHz, rotamers) δ: 0.97(m, 1H), 1.09(m, 1H), 1.43–1.47(d, 9H), 1.55–1.87(m, 8H), 2.07(m, 1H), 2.76(m, 1H), 3.16(m, 1H), 3.39(m, 1H), 3.54(m, 1H), 3.68(m, 1H), 3.88(m, 1H), 4.146(m, 1H), 7.30(d, 1H), 7.41 (m, 2H), 7.48(m, 1H) LCMS APCI$^+$ m/z 407 [MH]$^+$ and m/z 307 [MH-Boc]$^+$

Preparation 18 tert-butyl (3S)-3-(cycloheptylamino)pyrrolidine-1-carboxylate

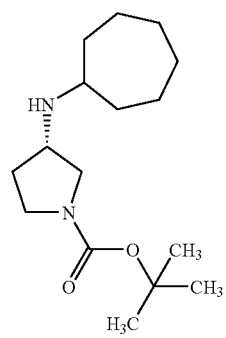

tert-butyl (3S)-3-(cycloheptylamino)pyrrolidine-1-carboxylate was prepared by a method similar to that described in preparation 14 using tert-butyl (3S)-3-aminopyrrolidine-1-carboxylate and cycloheptanone to yield the desired product, 4.54 g (100%).

$^1$HNMR(CD$_3$OD, 400 MHz) δ: 1.45(s, 12H), 1.57(m, 5H), 1.69(m, 3H), 1.89(m, 2H), 2.12(m, 1H), 2.71(m, 1H), 3.02(m, 1H), 3.26(m, 1H), 3.45(m, 2H), 3.59(m, 1H) MS APCI$^+$ m/z 283 [MH]$^+$

Preparation 19 tert-Butyl (3S)-3-[(2-chlorobenzoyl)(cycloheptyl)amino]pyrrolidine-1-carboxylate

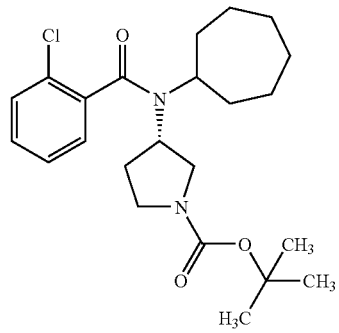

tert-Butyl-(3S)-3-[(2-chlorobenzoyl)(cycloheptyl)amino]pyrrolidine-1-carboxylate was prepared by a method similar to that described in preparation 2 (using Toluene as solvent, N-Methyl Morpholine as base, and heating the reaction mixture at 60° C. for 18 hours) using the amine of preparation 18 and 2-chlorobenzoyl chloride to yield the desired product, 1.27 g (90%).

MS APCI$^+$ m/z 421 [MH]$^+$ and m/z 321 [MH-Boc]$^+$

Preparation 20 tert-Butyl (3S)-3-{cycloheptyl[2-(trifluoromethyl)benzoyl]amino}pyrrolidine-1-carboxylate

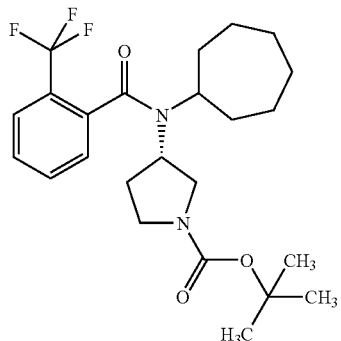

tert-Butyl-(3S)-3-{cyclohepty][2-(trifluoromethyl)benzoyl]amino}pyrrolidine-1-carboxylate was prepared by a method similar to that described in preparation 2 (using Toluene as solvent, N-Methyl Morpholine as base, and heating the reaction mixture at 60° C. for 18 hours) using the amine of preparation 18 and 2-(trifluoromethyl)benzoyl chloride to yield the desired product, 910 mg (57%).

MS APCI$^+$ m/z 455 [MH]$^+$ and m/z 355 [MH-Boc]$^+$

Preparation 21 tert-Butyl (3S)-3-{cyclohexyl[2-(trifluoromethyl)benzoyl]amino}pyrrolidine-1-carboxylate

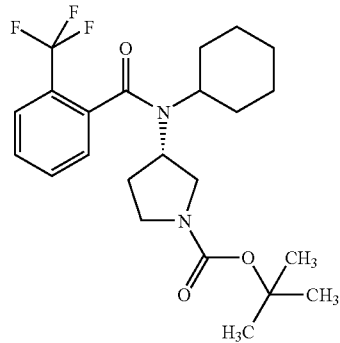

tert-Butyl-(3S)-3-{cyclohexyl[2-(trifluoromethyl)benzoyl]amino}pyrrolidine-1-carboxylate was prepared by a method similar to that described in preparation 2 (using Toluene as solvent, N-Methyl Morpholine as base, and heating the reaction mixture at 60° C. for 18 hours) using the amine of preparation 4 and 2-(trifluoromethyl)benzoyl chloride to yield the desired product, 860 mg (52%).

MS APCI$^+$ m/z 441 [MH]$^+$ and m/z 341 [MH-Boc]$^+$

Preparation 22 tert-Butyl (3S)-3{cyclopentyl[2-(trifluoromethyl)benzoyl]amino}pyrrolidine-1-carboxylate

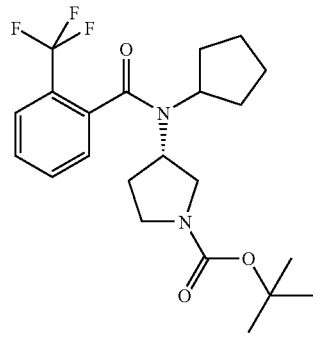

tert-Butyl-(3S)-3{cyclopentyl[2-(trifluoromethyl)benzoyl]amino}pyrrolidine-1-carboxylate was prepared by a method similar to that described in preparation 2 (using Toluene as solvent, N-Methyl Morpholine as base, and heating the reaction mixture at 60° C. for 18 hours) using the amine of preparation 1 and 2-(trifluoromethyl)benzoyl chloride to yield the desired product, 910 mg (54%).

$^1$HNMR(CDCl$_3$, 400 MHz, rotamers) δ: 1.43–1.47(brd, 11H), 1.55(m, 2H), 1.65(m, 1H), 1.76(m, 2H), 1.99(m, 2H), 2.35(m, 0.5H), 2.89(m, 0.5H), 3.05(m, 0.5H), 3.19(m, 0.5H), 3.39(m, 1H), 3.57(m, 1H), 3.69(m, 2H), 3.96(m, 1H), 7.24(m, 1H), 7.50(m, 1H), 7.57(m, 1H), 7.69(d, 1H) MS APCI$^+$ m/z 427 [MH]$^+$ and m/z 327 [MH-Boc]$^+$

Preparation 23 tert-Butyl (3S)-3-{[(1-methylcyclopropyl)carbonyl]amino}pyrrolidine-1-carboxylate

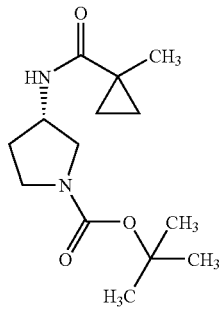

1-Methyl cyclopropane carboxylic acid (2.96 g, 29.54 mmol) was added to a solution of tert-butyl (3S)-3-aminopyrrolidine-1-carboxylate (5 g, 26.85 mmol) in dichloromethane (135 ml) at room temperature. Triethylamine (9.4 ml, 67.13 mmol) was then added. The reaction was cooled down to 0° C. and 2,4,6-tripropyl-1,3,5,2,4,6-trioxatriphosphinane 2,4,6-trioxide (50% in ethyl acetate, 17.4 ml, 29.54 mmol) was added. The mixture was stirred at room temperature for 1 hour and then concentrated under reduced pressure. The residue was diluted in dichloromethane (100 ml) and a 20% aqueous potassium carbonate solution (80 ml) added. The mixture was stirred at room temperature for 18 hours and the layers separated. The organic layer was washed with 20% potassium carbonate solution (50 ml), brine (80 ml), dried over magnesium sulfate, concentrated in vacuo and azeotroped with diethyl ether to provide the title compound as a white solid (6.815 g, 95%).

$^1$HNMR (CDCl$_3$, 400 MHz) δ: 0.52–0.54(m, 2H), 1.16–1.19(m, 2H), 1.29(s, 3H), 1.45(s, 9H), 1.81(brs, 1H), 2.14(m, 1H), 3.14(brs, 1H), 3.42(brs, 2H), 3.64(m, 1H), 4.44(m, 1H), 5.73(brs, 1H). MS APCI+ m/z 269 [MH]$^+$.

Preparation 24 tert-Butyl (3S)-3-{[(1-methylcyclopropyl)methyl]amino}pyrrolidine-1-carboxylate

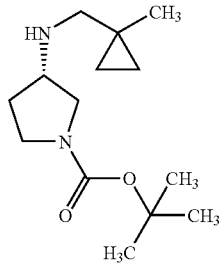

Borane (1M in tetrahydrofuran, 75 ml, 75 mmol) was added slowly to a solution of the compound of preparation 23 (6.815 g, 25.39 mmol) in tetrahydrofuran (75 ml) under nitrogen. The mixture was heated at reflux for 2 hours, then stirred at room temperature for 18 hours. Methanol was added carefully to quench the reaction mixture and then the mixture concentrated in vacuo. The residue was taken up in methanol (120 ml) and heated at reflux for 3 hours. Aqueous ammonium chloride was then added and the reaction mixture heated at reflux for 4 hours. The reaction was then concentrated in vacuo, the residue was partitioned between Ethyl Acetate and 1N aqueous NaOH, the aqueous phase was extracted once with Ethyl Acetate and the pooled organic phases were dried over Magnesium Sulfate, filtered and concentrated under reduced pressure. The crude product was purified by column chromatography on silica gel eluting with ethyl acetate:pentane (20:80 to 30:70) to yield the title product as a white solid (3.85 g, 60%).

$^1$HNMR (CD$_3$OD, 400 MHz) δ: 0.55–0.58(m, 2H), 0.62–0.64(m, 2H), 1.22(s, 3H), 1.46(s, 9H), 2.08(m, 1H), 2.36(m, 1H), 2.94(q, 2H), 3.36–3.41(m, 2H), 3.56(m, 1H), 3.74–3.86(m, 2H). MS APCI+ m/z 255 [MH]$^+$.

Preparation 25 tert-Butyl (3S)-3{(2,3-dichlorobenzoyl)[(1-methylcyclopropyl)methyl]amino}pyrrolidine-1-carboxylate

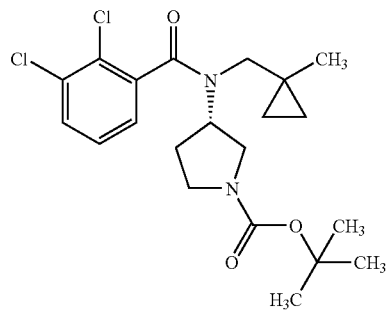

tert-Butyl(3S)-3-{(2,3-dichlorobenzoyl)[(1-methylcyclopropyl)methyl]amino}pyrrolidine-1-carboxylate was prepared by a method similar to that described in Preparation 2 using the amine of Preparation 24 and 2,3-dichlorobenzoyl chloride to yield the desired product (448 mg, 85%).

$^1$HNMR (DMSO-D$_6$, 400 MHz, rotamers) δ: 0.15–0.18 (m, 1.5H), 0.26–0.31(m, 1.5H), 0.42(m, 0.5H), 0.53(m, 1H), 0.88(d, 2H), 1.07(s, 1.5H), 1.33(s, 4H), 1.39(s, 5H), 2.05(m, 1H), 2.55(m, 0.5H), 2.82(m, 0.5H), 2.96 (m, 0.5H), 3.10–3.22(m, 2H), 3.31(m, 1H), 3.49–3.56(m, 1.5H), 3.65 (m, 0.5H), 4.23(m, 0.5H), 7.35(m, 1H), 7.42(m, 1H), 7.66 (m, 1H). MS APCI+ m/z 427 [MH]$^+$.

Preparation 26 tert-Butyl (3S)-3-{(3-chloro-2-methylbenzoyl)[(1-methylcyclopropyl)methyl]amino}pyrrolidine-1-carboxylate

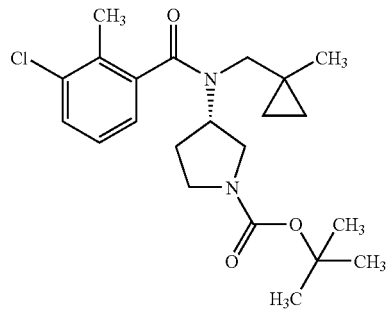

tert-Butyl (3S)-3-{(3-chloro-2-methylbenzoyl) [(1-methylcyclopropyl) methyl]amino}pyrrolidine-1-carboxylate was prepared by a method similar to that described in preparation 3 using the amine of Preparation 24 and 3-chloro-2-methyl benzoic acid to yield the desired product (300 mg, 60%).

$^1$HNMR (DMSO-D$_6$, 400 MHz, rotamers) δ: 0.18(m, 1H), 0.24–0.32(m, 2H), 0.51(m, 1H), 0.83(s, 2H), 1.06(s, 1H), 1.32(s, 4H), 1.39(s, 5H), 1.85(m, 0.5H), 2.04(m, 1H), 2.18(s, 2H), 2.22(s, 1H), 2.56 (m, 1H), 2.95(m, 1H), 3.09(m, 1H), 3.18–3.22(m, 2H), 3.48–3.55(m, 1.5H), 3.66(m, 0.5H), 4.22(m, 0.5H), 7.15(m, 1H), 7.26(t, 1H), 7.45(d, 1H). MS APCI+ m/z 407 [MH]+

Preparation 27 tert-Butyl (3S)-3-[(cyclobutylcarbonyl)amino]pyrrolidine-1-carboxylate

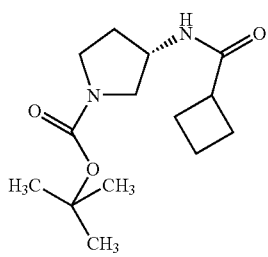

Cyclobutanecarbonylchloride (9 g, 76 mmol) was added to a solution of triethylamine (12.5 ml, 89.7 mmol) and tert-butyl (3S)-3-aminopyrrolidine-1-carboxylate (12.87 g, 69 mmol) in dichloromethane (385 ml) at room temperature under nitrogen. After stirring for 18 hours at room temperature, the reaction mixture was washed with water, dried over magnesium sulfate and concentrated in vacuo to yield the title product as a light brown glass, (17.4 g, 94%)
$^1$HNMR(400 MHz, CDCl$_3$) δ: 1.45 (s, 9H), 1.75–2.00 (m, 3H), 2.07–2.30 (m, 5H), 2.95 (m, 1H), 3.15 (m, 1H), 3.40 (m, 2H), 3.60 (m, 1H), 4.44 (m, 1H), 5.40 (brs, 1H)

Preparation 28 tert-butyl (3S)-3-{(cyclobutylmethyl)[2-(trifluoromethyl)benzoyl]amino}pyrrolidine-1-carboxylate

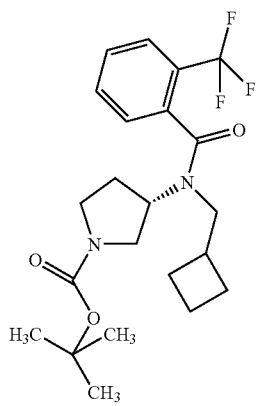

tert-butyl (3S)-3-[(cyclobutylmethyl)amino]pyrrolidine-1-carboxylate (0.80 g, 3.15 mmol) in toluene (10 ml) was treated with 2-(trifluoromethyl)benzoyl chloride (0.55 ml, 3.78 mmol) and triethylamine (0.88 ml, 6.3 mmol). The solution was stirred for 18 hours at room temperature and the solvent removed under reduced pressure. The crude product was purified by column chromatography on silica gel using a gradient of pentane:ethylacetate (4:1 by volume) changing to pentane:ethylacetate (1:1 by volume) to afford the title compound as a colorless oil (1.40 g, crude) which is used directly in the next step.

MS APCI+ m/z 427 [MH]+, 371 [MH-isobutylene]+, 327[MH-BOC]+

EXAMPLE 1

2,3-dichloro-N-cyclopentyl-N-[(3S)pyrrolidin-3-yl]benzamide hemi-edisylate

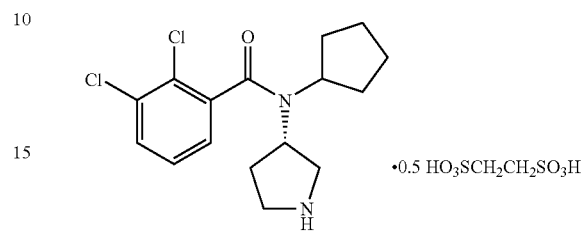

•0.5 HO$_3$SCH$_2$CH$_2$SO$_3$H

The Boc protected product of preparation 2 (46 g, 107 mmol) was dissolved in dichloromethane (85 ml) under nitrogen and the reaction mixture treated with trifluoroacetic acid (85 ml, 1 mol) added dropwise at 0° C. The reaction mixture was then stirred at room temperature for 4 hours, evaporated under reduced pressure, azeotroped twice with toluene and concentrated in vacuo. The residue was taken up in dichloromethane (400 ml) and washed with 1M aqueous sodium hydroxide (200 ml). The organic phase was separated, dried over magnesium sulfate and concentrated in vacuo. The residue was azeotroped with ethyl acetate (10×) and then dried under vacuum to yield the free base of the title product as a gum, 34 g (97%). A portion of this product (24 g, 70 mmol) in isopropanol (400 ml) was treated with a solution of ethane-disulfonic acid hydrate (6.65 g, 35 mmol) in isopropanol (70 ml). The solvent was removed in vacuo and the residue azeotroped with ethyl acetate to afford a beige foam which was crystallized from isopropanol/diisopropyl ether to yield an off-white solid (23.3 g). The solid was recrystallised from isopropanol/methanol (700 ml of isopropanol and minimal amount of methanol required to achieve solubility) and dried under high vacuum to provide the title compound as a white solid (13.94 g).
$^1$HNMR (CD$_3$OD, 400 MHz) δ: 1.40–1.74(m, 7H), 1.92 (m, 1H), 2.52(m, 2H), 3.24(s, 2H), 3.30(m, 1H), 3.56(m, 1H), 3.78(m, 3H), 4.33(m, 1H), 7.35(dd, 1H), 7.42(t, 1H), 7.63(d, 1H) MS APCI+ m/z 327 [MH+] LC-MS ELSD m/z 327 100% Microanalysis: Found: C, 47.37; H, 5.59; N, 6.47. C$_{16}$H$_{20}$Cl$_2$N$_2$O. 0.5C$_2$H$_6$O$_6$S$_2$. 0.5H$_2$O requires C, 47.34; H, 5.61; N, 6.49%.

EXAMPLE 2

2,3-dichloro-N-cyclopentyl-4-fluoro-N-[(3S)-pyrrolidin-3-yl]benzamide hydrochloride

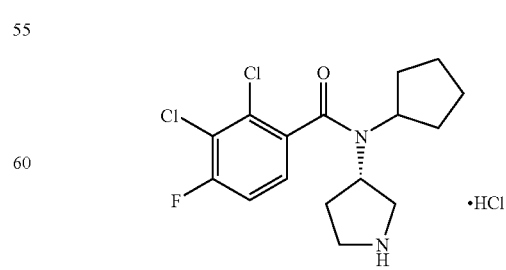

•HCl

Hydrogen Chloride (4M in 1,4-dioxane, 37 ml, 148 mmol) was added to a solution of product from preparation 3 (6.65 g, 14.93 mmol) in dichloromethane (40 ml). After stirring at room temperature for 18 hours, the solvent was removed by evaporation under reduced pressure to produce a solid, which was triturated with ether to yield the title product (5.5 g) as a white solid.

$^1$HNMR (CD$_3$OD, 400 MHz) δ: 1.54 (m, 4H), 1.73 (m, 3H), 1.92(m, 1H), 2.52 (m, 2H), 3.25 (m, 1H), 3.52 (m, 1H), 3.78 (m, 3H), 4.32 (m, 1H), 7.37 (m, 2H) MS APCI$^+$ m/z 345 [M]$^+$

EXAMPLE 3

3-chloro-N-cyclopentyl-2-methyl-N-[(3S)-pyrrolidin-3-yl]benzamide hydrochloride

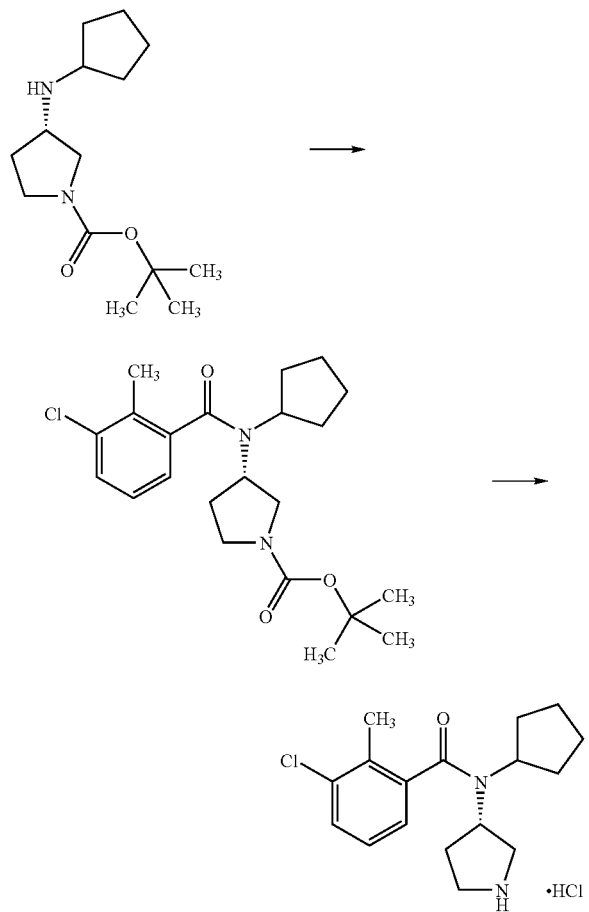

tert-Butyl(3S)-3-[cyclopentyl(3-chloro-2-methylbenzoyl)amino]pyrrolidine-1-carboxylate was prepared by a method similar to that described in preparation 3 using the amine of preparation 1 and 3-chloro-2-methyl benzoic acid to yield the desired product, 606 mg (crude).

MS APCI+ m/z 407 [MH]$^+$.

3-chloro-N-cyclopentyl-2-methyl-N-[(3S)-pyrrolidin-3-yl]benzamide hydrochloride was prepared from the foregoing compound by a method similar to that described in example 2 to yield the title product as a solid, 199 mg (47%).

$^1$HNMR (CD$_3$OD, 400 MHz) δ: 1.44–1.60(m, 4H), 1.79 (m, 4H), 2.33(d, 3H), 2.44–2.54(m, 2H), 3.24(m, 1H), 3.54(m, 1H), 3.72(m, 1H), 3.80(m, 2H), 4.31(m, 1H), 7.16 (dd, 1H), 7.28(t, 1H), 7.47(d, 1H) LCMS ELSD/APCI+ m/z 307 [MH]$^+$ 100%. Microanalysis: Found: C, 58.25; H, 7.20; N, 7.92%. Calc. for C$_{17}$H$_{23}$ClN$_2$O.HCl.0.4H$_2$O: C, 58.26; H, 7.13; N, 7.99%.

EXAMPLE 4

N-cyclopentyl-3-fluoro-2-methyl-N-[(3S)-pyrrolidin-3-yl]benzamide hydrochloride

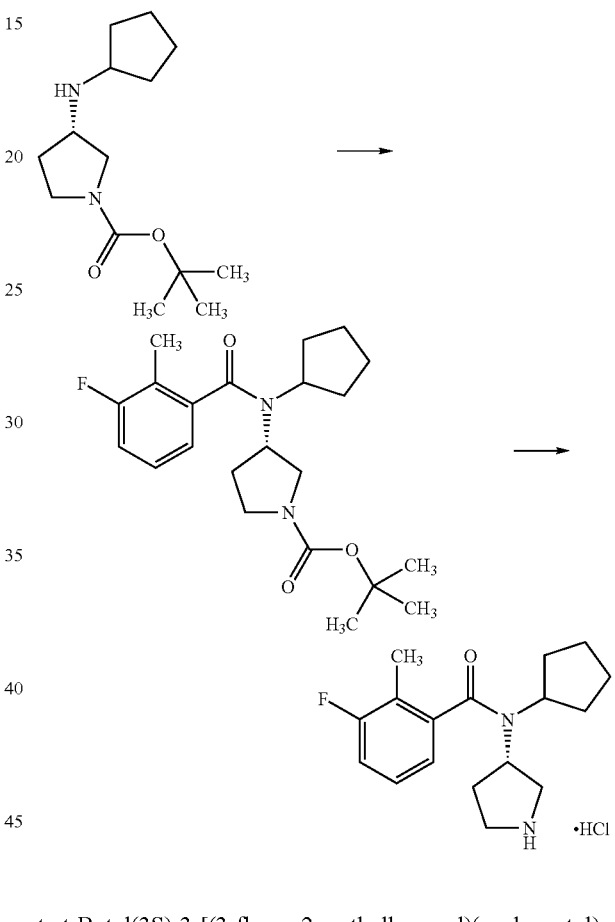

tert-Butyl(3S)-3-[(3-fluoro-2-methylbenzoyl)(cyclopentyl)amino]pyrrolidine-1-carboxylate was prepared by a method similar to that described in preparation 3 using the amine of preparation 1 and 3-fluoro-2-methyl benzoic acid to yield the desired product, 639 mg (crude).

MS APCI+ m/z 391 [MH]$^+$.

N-cyclopentyl-3-fluoro-2-methyl-N-[(3S)-pyrrolidin-3-yl]benzamide hydrochloride was prepared from the foregoing compound by a method similar to that described in example 2 to yield the title product as a solid, 182 mg (46%).

$^1$HNMR (CD$_3$OD, 400 MHz) δ: 1.49–1.63(m, 4H), 1.78 (m, 4H), 2.22(d, 3H), 2.49(m, 2H), 3.25(m, 1H), 3.55(m, 1H), 3.74(m, 1H), 3.87(m, 2H), 4.31(m, 1H), 7.03(dd, 1H), 7.14(t, 1H), 7.31(q, 1H) MS APCI+ m/z 291 [MH]+LCMS ELSD/APCI+ m/z 291 [MH]$^+$ 100%. Microanalysis: Found: C, 61.18; H, 7.51; N, 8.25%. Calc. for C$_{17}$H$_{23}$FN$_2$O.HCl.0.39H$_2$O: C, 61.16; H, 7.48; N, 8.39%.

EXAMPLE 5

2-chloro-N-cyclopentyl-3-fluoro-N-[(3S)-pyrrolidin-3-yl]benzamide hydrochloride

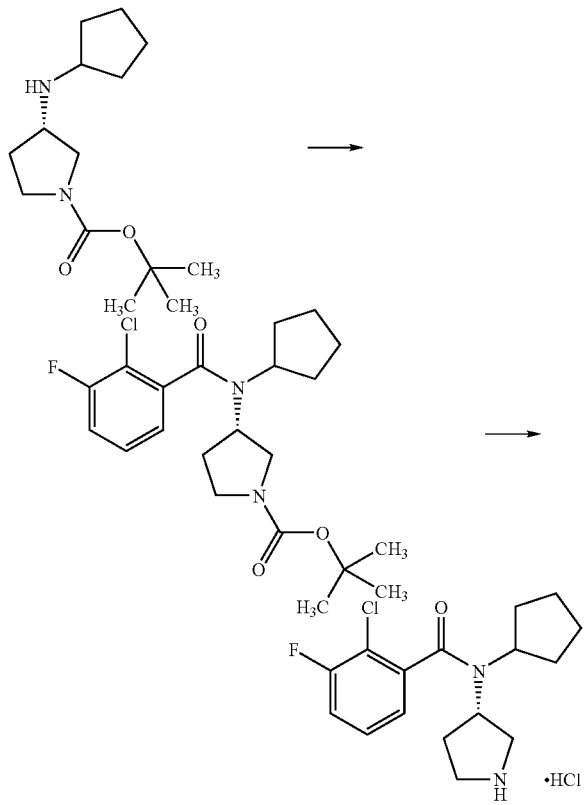

tert-Butyl(3S)-3-[(2-chloro-3-fluorobenzoyl)(cyclopentyl)amino]pyrrolidine-1-carboxylate was prepared by a method similar to that described in preparation 3 using the amine of preparation 1 and 2-chloro-3-fluoro benzoic acid to yield the desired product.

2-chloro-N-cyclopentyl-3-fluoro-N-[(3S)pyrrolidin-3-yl]benzamide hydrochloride was prepared from the foregoing compound by a method similar to that described in example 2 to yield the title product as a solid, 62 mg (15%).

$^1$HNMR (CD$_3$OD, 400 MHz) δ: 1.44–1.63(m, 4H), 1.73 (m, 3H), 1.92(m, 1H), 2.52(m, 2H), 3.24(m, 1H), 3.58(m, 1H), 3.80(m, 3H), 4.32(m, 1H), 7.19(dd, 1H), 7.35(t, 1H), 7.45(m, 1H). LCMS ELSD/APCI+ m/z 311 [MH]$^+$ 100%. Microanalysis: Found: C, 53.68; H, 6.30; N, 7.71%. Calc. for C$_{16}$H$_{20}$ClFN$_2$O.HCl.0.6H$_2$O: C, 53.67; H, 6.25; N, 7.82%.

EXAMPLE 6

2,3-dichloro-N-cyclohexyl-N-[(3S)-pyrrolidin-3-yl]benzamide hydrochloride

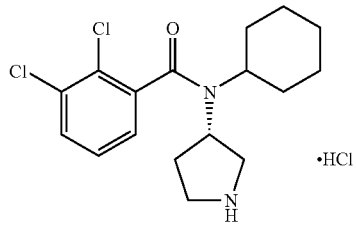

2,3-dichloro-N-cyclohexyl-N-[(3S)-pyrrolidin-3-yl]benzamide hydrochloride was prepared from the compound of preparation 5 by a method similar to that described in example 2 to yield the title product as a solid, 3.95 g (89%).

$^1$HNMR (CD$_3$OD, 400 MHz) δ: 1.02–1.10(m, 3H), 1.56–1.81(m, 7H), 2.46(m, 2H), 3.13(m, 1H), 3.25(m, 1H), 3.48(m, 1H), 3.73(m, 1H), 3.81 (m, 1H), 4.45(m, 1H), 7.32(dd, 1H), 7.43(t, 1H), 7.66(d, 1H). MS APCI+ m/z 341 [MH]$^+$.

EXAMPLE 7

2-chloro-N-cyclohexyl-3-fluoro-N-[(3S)-pyrrolidin-3-yl]benzamide hydrochloride

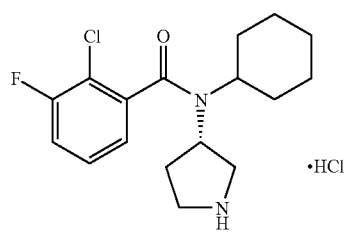

2-chloro-N-cyclohexyl-3-fluoro-N-[(3S)-pyrrolidin-3-yl]benzamide hydrochloride was prepared from the compound of preparation 6 by a method similar to that described in example 2 to yield the title product as a solid, 118 mg (88%).

$^1$HNMR (CD$_3$OD, 400 MHz) δ: 0.99–1.12(m, 3H), 1.56–1.91(m, 7H), 2.47(m, 2H), 3.16–3.22(m, 2H), 3.50(m, 1H), 3.71 (m, 1H), 3.81 (m, 1H), 4.45(m, 1H), 7.21 (dd, 1H), 7.37(t, 1H), 7.46(m, 1H). MS APCI+ m/z 325 [MH]$^+$. Microanalysis: Found: C, 54.87; H, 6.55; N, 7.30%. Calc. for C$_{17}$H$_{22}$ClFN$_2$O.HCl.0.6H$_2$O: C, 54.88; H, 6.56; N, 7.53%.

EXAMPLE 8

N-cyclohexyl-3-fluoro-2-methyl-N-[(3S)-pyrrolidin-3-yl]benzamide hydrochloride

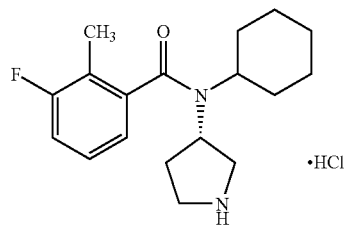

N-cyclohexyl-3-fluoro-2-methyl-N-[(3S)-pyrrolidin-3-yl]benzamide hydrochloride was prepared from the compound of preparation 7 by a method similar to that described in example 2 to yield the title product as a solid, 45 mg (85%).

$^1$HNMR (CD$_3$OD, 400 MHz) δ: 0.99–1.17(m, 3H), 1.54–1.77(m, 7H), 2.20(d, 3H), 2.47(m, 2H), 3.23(m, 2H), 3.48(m, 1H), 3.70(m, 1H), 3.81(m, 1H), 4.43(m, 1H), 7.03 (dd, 1H), 7.16(t, 1H), 7.31(q, 1H). MS APCI+ m/z 305 [MH]$^+$ LCMS ELSD m/z 305 [MH]$^+$ 100%. Microanalysis: Found: C, 60.87; H, 7.80; N, 7.59%. Calc. for C$_{18}$H$_{25}$FN$_2$O.HCl.0.79H$_2$O: C, 60.88; H, 7.83; N, 7.89%.

EXAMPLE 9

2,3-dichloro-N-cyclobutyl-N-[(3S)-pyrrolidin-3-yl]benzamide hydrochloride

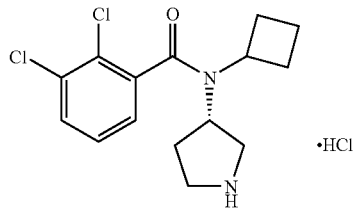

2,3-dichloro-N-cyclobutyl-N-[(3S)-pyrrolidin-3-yl]benzamide hydrochloride was prepared from the compound of preparation 9 by a method similar to that described in example 2 to yield the title product as a solid, 311 mg (99%).

$^1$HNMR (CD$_3$OD, 400 MHz) δ: 1.56(m, 1H), 1.70(m, 1H), 2.00(m, 1H), 2.13(m, 1H), 2.23–2.30(m, 2H), 2.46(m, 1H), 2.54(m, 1H), 3.26(m, 1H), 3.54(m, 1H), 3.73–3.81 (m, 2H), 4.00(m, 1H), 4.71 (m, 1H), 7.31 (m, 1H), 7.43(t, 1H), 7.66(d, 1H). MS APCI+ m/z 313 [MH]$^+$.

EXAMPLE 10

N-cyclobutylmethyl-2,3-dichloro-N-[(3S)-pyrrolidin-3-yl]benzamide hydrochloride

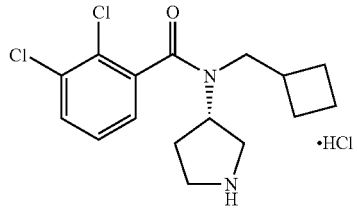

N-cyclobutylmethyl-2,3-dichloro-N-[(3S)-pyrrolidin-3-yl]benzamide hydrochloride was prepared from the compound of preparation 12 by a method similar to that described in example 1 to yield the title product as a gum, 55 mg (68%).

$^1$HNMR (CD$_3$OD, 400 MHz) δ: 1.55–1.70(m, 3H), 1.85–2.03(m, 3H), 2.54(m, 3H), 3.15(m, 1H), 3.26(m, 2H), 3.50(m, 1H), 3.76(m, 2H), 4.30(m, 1H), 7.38(m, 1H), 7.43(t, 1H), 7.66(d, 1H). LCMS UV/ESI+ m/z 327 [MH]$^+$. Microanalysis: Found: C, 50.83; H, 5.90; N, 7.42%. Calc. for C$_{16}$H$_{20}$Cl$_2$N$_2$O.HCl.0.75H$_2$O: C, 50.94; H, 6.01; N, 7.43%.

EXAMPLE 11

2,3-dichloro-N-(cyclopropylmethyl)-N-[(3S)-pyrrolidin-3-yl]benzamide hydrochloride

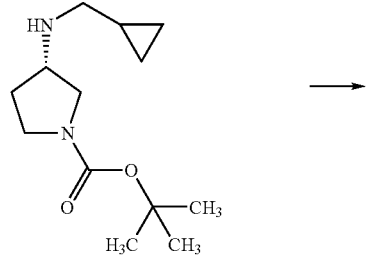

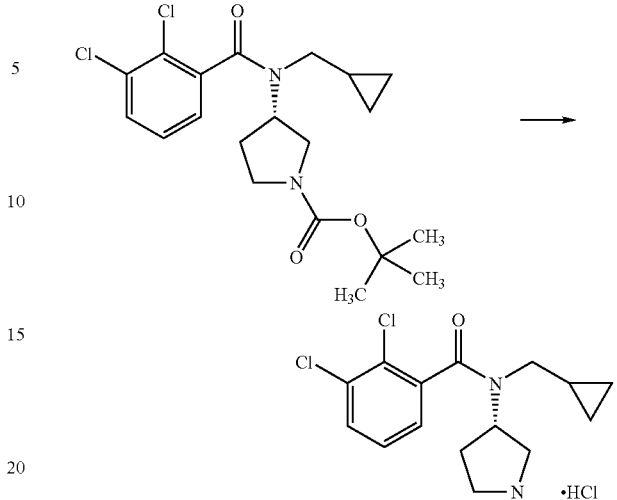

tert-Butyl(3S)-3-[cyclopropylmethyl(2,3-dichlorobenzoyl)amino]pyrrolidine-1-carboxylate was prepared by a method similar to that described in preparation 1 using the amine of preparation 13 and 2,3-dichlorobenzoyl chloride to yield the desired product (crude).

MS APCI+ m/z 413 [MH]$^+$ and m/z 313 [MH-Boc]$^+$ 2,3-dichloro-N-(cyclopropylmethyl)-N-[(3S)-pyrrolidin-3-yl]benzamide hydrochloride was prepared from the foregoing compound by a method similar to that described in example 1, purification by chromatography, and formation of the hydrogen chloride salt, yielding the title product as a gum, 393 mg (77%).

$^1$HNMR (CD$_3$OD, 400 MHz) δ: 0.09(m, 2H), 0.502(m, 2H), 0.88(m, 1H), 2.47–2.54(m, 2H), 3.01(m, 2H), 3.21(m, 1H), 3.50(m, 1H), 3.76(m, 2H), 4.42(m, 1H), 7.36(m, 2H), 7.59(d, 1H). LCMS ELSD/APCI+ m/z 313 [MH]$^+$ 100%. Microanalysis: Found: C, 49.52; H, 5.65; N, 7.45%. Calc. for C$_{15}$H$_{18}$Cl$_2$N$_2$O.HCl.0.78H$_2$O: C, 49.53; H, 5.70; N, 7.70%.

EXAMPLE 12

2,3-dichloro-N-[(3S)-pyrrolidin-3-yl]-N-tetrahydro-2H-pyran-4-ylbenzamide

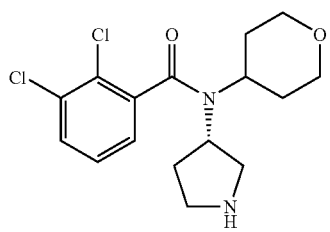

2,3-dichloro-N-[(3S)-pyrrolidin-3-yl]-N-tetrahydro-2H-pyran-4-ylbenzamide was prepared from the compound of preparation 15 by a method similar to that described in example 2 (the free base was obtained by column chromatography on silica gel using a gradient of Methylene Chloride:Methanol:Aqueous Ammonia (100:0:0 by volume) changing to Methylene Chloride:Methanol:Aqueous Ammonia (100:10:1 by volume), to afford the title compound as a colorless oil using to yield the title product as a gum, 120 mg (77%).

$^1$HNMR (CD$_3$OD, 400 MHz) δ: 1.58(m, 1H), 1.74(m, 1H), 1.89–1.97(m, 2H), 2.28(m, 2H), 2.96(m, 1.5H), 3.11–3.20(m, 3H), 3.45–3.53(m, 3H), 3.92(m, 1.5H), 4.03 (m, 0.5H), 4.20(m, 0.5H), 7.32(dd, 1H), 7.42(t, 1H), 7.64(d, 1H) MS APCI+ m/z 343 [MH]+

EXAMPLE 13

2-chloro-N-cyclopentyl-N-[(3S)-pyrrolidin-3-yl]benzamide

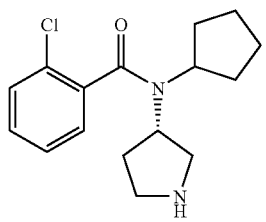

2-chloro-N-cyclopentyl-N-[(3S)-pyrrolidin-3-yl]benzamide was prepared from the compound of preparation 16 by a method similar to that described in example 1 to yield the title product, 640 mg (74%).

$^1$HNMR (CD$_3$OD, 400 MHz) δ: 1.43(m, 2H), 1.61(m, 2H), 1.72(m, 3H), 1.92(m, 2H), 2.38(m, 2H), 3.09(q, 1H), 3.57–3.65(m, 2H), 3.79(m, 1H), 4.15(m, 1H), 7.33(m, 1H), 7.43(m, 2H), 7.49(m, 1H) MS APCI+ m/z 293 [MH$^+$]

EXAMPLE 14

2-chloro-N-cyclohexyl-N-[(3S)pyrrolidin-3-yl]benzamide

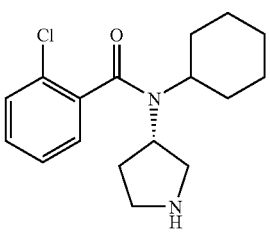

2-chloro-N-cyclohexyl-N-[(3S)-pyrrolidin-3-yl]benzamide was prepared from the compound of preparation 17 by a method similar to that described in example 1 to yield the title product, 685 mg (83%).

$^1$HNMR (CD$_3$OD, 400 MHz) δ: 0.98–1.13(brm, 3H), 1.54–1.88(brm, 7H), 2.44(m, 2H), 3.19(m, 2H), 3.44(q, 1H), 3.66(m, 1H), 3.78(m, 1H), 4.41(m, 1H), 7.34–7.52(brm, 4H). MS APCI+ m/z 307 [MH]$^+$.

EXAMPLE 15

2-chloro-N-cycloheptyl-N-[(3S)-pyrrolidin-3-yl]benzamide

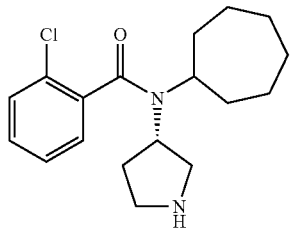

2-chloro-N-cycloheptyl-N-[(3S)-pyrrolidin-3-yl]benzamide was prepared from the compound of preparation 19 by a method similar to that described in example 1 to yield the title product, 785 mg (81%).

$^1$HNMR (CD$_3$OD, 400 MHz) δ: 1.27(m, 3H), 1.44(m, 3H), 1.62(m, 1H), 1.75–1.92(m, 5H), 2.49(m, 2H), 3.22(m, 2H), 3.49(q, 1H), 3.70(m, 1H), 3.81 (m, 1H), 4.36(m, 1H), 7.35–7.52(brm, 4H). MS APCI+ m/z 321 [MH]$^+$.

EXAMPLE 16

N-cycloheptyl-N-[(3S)-pyrrolidin-3-yl]-2-(trifluoromethyl)benzamide

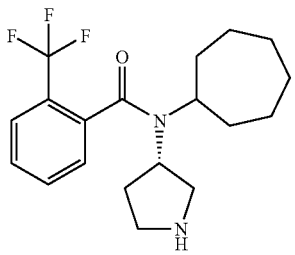

N-cycloheptyl-N-[(3S)-pyrrolidin-3-yl]-2-(trifluoromethyl)benzamide was prepared from the compound of preparation 20 by a method similar to that described in example 1 to yield the title product, 502 mg (72%).

$^1$HNMR (CD$_3$OD, 400 MHz) δ: 1.19(m, 2H), 1.32(m, 1H), 1.42(m, 3H), 1.65–1.81(m, 6H), 2.45(m, 2H), 3.24(m, 2H), 3.48(t, 1H), 3.56(m, 0.5H), 3.76(m, 1.5H), 4.35(m, 1H), 7.49(dd, 1H), 7.69(m, 1H), 7.75(m, 1H), 7.81 (m, 1H). MS APCI+ m/z 355 [MH]$^+$.

EXAMPLE 17

N-cyclohexyl-N-[(3S)-pyrrolidin-3-yl]-2-(trifluoromethyl)benzamide

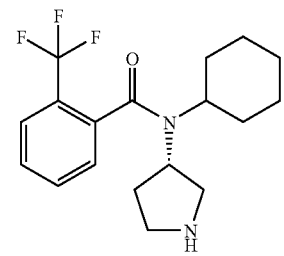

N-cyclohexyl-N-[(3S)-pyrrolidin-3-yl]-2-(trifluoromethyl)benzamide was prepared from the compound of preparation 21 by a method similar to that described in example 1 to yield the title product, 460 mg (69%).

$^1$HNMR (CD$_3$OD, 400 MHz) δ: 0.95–1.08(m, 3H), 1.52–1.73(m, 7H), 2.08(m, 1H), 2.20(m, 1H), 2.79(m, 1H), 2.96(m, 1H), 3.06(m, 1H), 3.21 (dd, 0.5H), 3.37(m, 1.5H), 4.06(m, 1H), 7.42(dd, 1H), 7.65(m, 1H), 7.72(m, 1H), 7.79(m, 1H). MS APCI+ m/z 341 [MH]$^+$.

EXAMPLE 18

N-cyclopentyl-N-[(3S>pyrrolidin-3-yl]-2-(trifluoromethyl)benzamide

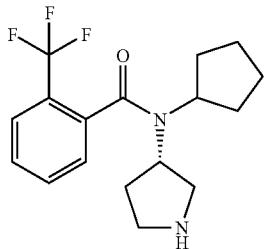

N-cyclopentyl-N-[(3S)-pyrrolidin-3-yl]-2-(trifluoromethyl)benzamide was prepared from the compound of preparation 22 by a method similar to that described in example 1 to yield the title product, 690 mg (99%).

$^1$HNMR (CD$_3$OD, 400 MHz) δ: 1.44(m, 2H), 1.59(m, 2H), 1.73(m, 4H), 2.47(m, 2H), 3.24(m, 1H), 3.53(m, 1.5H), 3.76(m, 2.5H), 4.29(m, 1H), 7.46(dd, 1H), 7.66(m, 1H), 7.74(m, 1H), 7.80(m, 1H). MS APCI+ m/z 327 [MH]$^+$.

EXAMPLE 19

2,3-Dichloro-N-[(1-methylcyclopropyl)methyl]-N-[(3S)-pyrrolidin-3-yl]benzamide hydrochloride

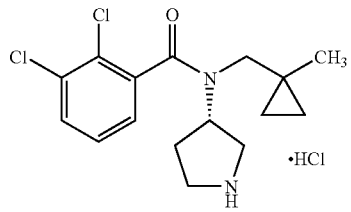

2,3-Dichloro-N-[(1-methylcyclopropyl)methyl]-N-[(3S)-pyrrolidin-3-yl]benzamide hydrochloride was prepared from the compound of preparation 25 by a method similar to that described in Example 2 to yield the title product as a solid (269 mg, 100%).

$^1$HNMR (CD$_3$OD, 400 MHz) δ: 0.25–0.32(m, 2H), 0.44 (m, 1H), 0.50(m, 0.5H), 0.60(m, 0.5H), 0.98(s, 3H), 2.50–2.61(m, 2H), 2.95(dd, 1H), 3.24–3.36(m, 2H), 3.57(m, 1H), 3.75–3.87(m, 2H), 4.52(m, 1H), 7.36–7.45(m, 2H), 7.63(d, 1H). MS APCI+ m/z 327 [MH]$^+$.

EXAMPLE 20

3-chloro-2-methyl-N-[(1-methylcyclopropyl)methyl]-N-[(3S)pyrrolidin-3-yl]benzamide hydrochloride

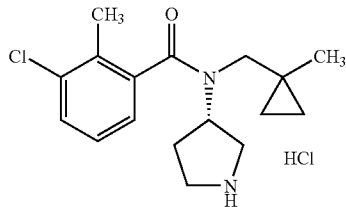

3-Chloro-2-methyl-N-[(1-methylcyclopropyl)methyl]-N-[(3S)-pyrrolidin-3-yl]benzamide hydrochloride was prepared from the compound of Preparation 26 by a method similar to that described in Example 2 to yield the title product as a solid (310 mg, 90%).

$^1$HNMR (CD$_3$OD, 400 MHz) δ: 0.29–0.42(m, 3.5H), 0.51(m, 0.5H), 0.96(s, 3H), 2.31 (d, 3H), 2.50(m, 1H), 2.59(m, 1H), 3.02(d, 0.5H), 3.15(q, 1H), 3.25–3.32(m, 1.5H), 3.59(m, 1H), 3.78–3.83(m, 2H), 4.51(brs, 1H), 7.21 (m, 1H), 7.29(t, 1H), 7.47(d, 1H). MS APCI+ m/z 307 [MH]$^+$.

EXAMPLE 21

N-(cyclobutylmethyl)-N-[(3S)-pyrrolidin-3-yl]-2-(trifluoromethyl)benzamide hydrochloride

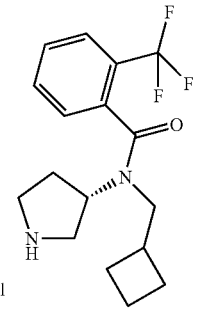

Tert-butyl (3S)-3-{(cyclobutylmethyl) [2-(trifluoromethyl) benzoyl]amino}pyrrolidine-1-carboxylate from preparation 28 (1.40 g, 3.3 mmol) was dissolved in 4N hydrogen chloride in Dioxane. The solution was stirred for 1 hour and the solvent removed under reduced pressure. The residue was dissolved in water and the solution washed with ether. The aqueous phase was basified by adding aqueous NaOH and extracted with ether. This ether phase was dried over Magnesium Sulfate, filtered and the solvent removed under reduced pressure to afford a gum, which was treated with 2N hydrogen chloride in ether, to afford 0.99 g (86%) of the title compound as a white foam.

$^1$HNMR(400 MHz, CD$_3$OD) δ:1.61–1.72 (m, 3H), 1.92–2.03 (m, 3H), 2.45 (m, 1H), 2.59 (m, 2H), 3.14 (m, 1H), 3.26 (m, 2H), 3.55 (m, 1H), 3.68–3.82 (m, 2H), 4.34 (m, 1H), 7.54 (m, 1H), 7.72 (m, 1H), 7.80 (m, 1H), 7.85 (m, 1H). LCMS APCI+ m/z 327[MH]$^+$

EXAMPLE 22

The NRI Ki and the SRI Ki of the compounds of Examples 1 to 21 were determined as follows. A selection of the results are set out below in Table 1. All of the Example compounds exhibited an NRI Ki and an SRI Ki of less than 100 nM.

Biological Activity

The compounds were tested for biological activity by their ability to inhibit binding of selective radioligands at the human serotonin and noradrenaline transporters (SERT and NET, respectively), using scintillation proximity assay (SPA) technology. The SPA binding was performed using cellular membrane preparations prepared from cell lines expressing human cDNA encoding either SERT or NET (hSERT, hNET), using the radioligands $^3$H-citalopram and $^3$H-nisoxetine.

i) Cell Culture Methodology

Human embryonic kidney cells (HEK-293) expressing each transporter were maintained as a continuous culture, using standard cell culture techniques, in 50 mL of growth medium (see Media and Buffers for composition) in 225 cm$^2$ flasks, at 37° C. in a humidified atmosphere with 5% $CO_2$ present. Cells were passaged from a 90% confluent monolayer at a ratio of 1:3–1:4.

For cell harvesting, the growth medium was removed from the monolayer and the cells were incubated with cell dissociation solution (Sigma) until showing signs of dissociation. The cells were subsequently knocked from the base of the flask and pelleted by centrifugation for storage (frozen at −80° C.) prior to further use.

ii) Cellular Membrane Preparation

Cell pellets were thawed on ice and resuspended in 3 mL of membrane preparation buffer (see Media and Buffers for composition) per 1 mL of packed cell volume, using a vortex mixer to disperse the cell pellet. After incubation on ice for 10 minutes, the suspension was homogenised for four individual 10 second intervals using a hand-held homogeniser. The homogenate was then centrifuged at 1075×g for 20 minutes at 4° C.

The supernatants were then collected and retained. Initial cell & nuclei pellets (P1) were subsequently rehomogenised and centrifuged using the conditions cited above, and the supernatants collected and pooled with those retained from the first spin.

The pooled supernatants were centrifuged at 35000×g for 30 minutes at 4° C., and the supernatants discarded. The pellets (P2) were then resuspended in 1 mL of membrane preparation buffer per 1 mL of the original packed cell volume. Protein concentrations were then measured and the membrane suspension was finally frozen in aliquots of set volume and stored at −80° C. prior to use in assays.

iii) Assay Methodology

A. Determination of Optimal Assay Conditions for Individual Membrane Batches

The specific SPA bead type differed for each transporter, wheat germ agglutinin-coated yttrium silicate (YSi WGA) SPA beads were used for hSERT and WGA-coated polyvinyltoluene (PVT WGA) SPA beads for hNET assays. For each batch of membrane used, optimal concentrations of bead and membrane were determined Tritiated radioligands specific to each transporter ($^3$H-citalopram for hSERT and $^3$H-nisoxetine for hNET) were used. The assay free radioligand concentration was expressed as a percentage of the total free radioligand concentration to give an estimate of the radioligand depletion. The radioligand depletion in assays for both transporters was less than 30% to ensure that there was sufficient radioligand available for binding. The ligand depletion value was also used for selecting the optimal assay conditions when using new batches of membranes.

The affinity of the specific radioligand for the respective transporter was determined for each membrane batch at the selected protein and bead concentrations. This was achieved by the determination of the $K_D$, the concentration of free radioligand at which 50% of the transporter binding sites were occupied.

The mean $K_D$ for a radioligand at a batch of membranes was determined from data from a minimum of three separate assays. The mean $K_D$ was subsequently used for all assays using the membrane batch profiled to enable determination of $K_i$ values of compounds studied using the method determined by Cheng and Prussoff (Cheng Y C and Prusoff W H. Relationship between the inhibition constant ($K_i$) and the concentration of inhibitor which causes 50% inhibition of an enzymatic reaction. Biochem Pharmacol 1973; 22:2099–3108.)

B. Assay Protocol

Bead/Membrane Complex Preparation

The required amount of membrane was thawed on ice and added to a predetermined volume of bead suspension in assay buffer. The beads were then pre-coupled by incubating the predetermined protein quantity per mg of bead on a shaker at a temperature of 4° C. for 2 hours.

Subsequently, the bead/membrane complex was spun down at 865×g for 5 minutes. The resulting pellet was resuspended in assay buffer and this spin/wash step then repeated. The final pellet was then resuspended in assay buffer at the specific concentration required for the final assay.

Ligand Preparation

An aliquot of [$^3$H]-radioligand stock was diluted in assay buffer to give a pre-determined final assay concentration less than the equilibrium dissociation constant ($K_D$) value.

Compound Plate Preparation

All test compounds were prepared at a concentration of 4 mM in 100% dimethyl sulphoxide (DMSO) from dry samples. Compounds were diluted in 0.75% DMSO in ddH$_2$O to give appropriate test concentrations in a 384 well plate to give a final volume of 20 µL.

The same volume of assay buffer was added to specific wells of the plate to enable subsequent measurement of total radioligand binding. Furthermore, 20 µL a high concentration of compound specific to each transporter assay was subsequently added to predetermined wells to determine non-specific binding (NSB). Fluoxetine (10 µM final assay concentration) was used for hSERT and desipramine (40 µM final assay concentration) for hNET.

For each individual transporter assay, 20 µL of the prepared specific radioligand was added to each well of the final assay plates (containing compound solutions). Subsequently, 20 µL of the corresponding bead/membrane complex was added to each well of the final assay plate, ensuring that the suspension was mixed well. The plates were then sealed and incubated, with shaking, for 1 hour at room temperature. The plates were subsequently incubated for an additional 6 hours, with dark adaptation, prior to reading.

C. Data Analysis

The assay window (specific binding) per plate was calculated by subtracting the mean NSB readings (in counts per minute, or cpm) from the mean of total binding readings. Subsequently the cpm read per well (with mean NSB subtracted) were expressed as a percentage of the plate window to determine the amount of radioligand bound to the transporter.

These values were plotted against the concentration of the compound tested and a sigmoidal inhibitory concentration effect curve was fitted to the data using a four-parameter logisitic equation and free-fitting parameters to give an $IC_{50}$ value (the concentration of compound required to inhibit 50% of the specific binding at the neurotransmitter transporter).

The inhibitory dissociation constant ($K_i$) value was then calculated from the $IC_{50}$ value using the Cheng-Prusoff equation Following determination of individual $K_i$ values for compounds tested, an overall geometric mean was calculated together with 95% confidence intervals and n values, where n is the total number of individual $K_i$ values. The resulting $K_i$ data of compounds, Examples 1–18, can be seen in Table 1.

iv) Media and Buffers hSERT Cell Growth Medium
DMEM, 10% (w/v) dialysed FCS
2 mM L-glutamine (diluted from 200 mM stock)
25 mM HEPES (diluted from 1 M stock)
250 µg/mL genetecin hNET Cell Growth Medium
DMEM, 10% (w/v) FCS
2 mM L-glutamine (diluted from 200 mM stock)
25 mM HEPES (diluted from 1 M stock)
250 µg/mL genetecin Membrane Preparation Buffer
20 mM HEPES (diluted from 1 M stock with $ddH_2O$), pH 7.4 at room temperature, stored at 4° C. Prior to use, one complete protease inhibitor tablet was dissolved per 50 mL of buffer.

Assay Buffer (1.5× Final Assay Concentration)
30 mM HEPES (diluted from 1 M stock with $ddH_2O$) and 180 mM NaCl (diluted from 5 M stock with $ddH_2O$), pH 7.4 at room temperature, stored at 4° C.

TABLE 1

| Compound | SRI Ki (nM) | NRI Ki (nM) |
|---|---|---|
| 1 | 5 | 15 |
| 6 | 9 | 11 |
| 14 | 11 | 9 |
| 20 | 3 | 14 |

The compounds can also be tested in specific disease models, such as the pain models as follows:

Neuropathic Pain

The activity of a compound in the treatment of neuropathic pain may be measured according to the following test protocol.

Animals: Male Sprague Dawley rats are housed in appropriately sized groups. All animals are kept under a 12 h light/dark cycle (lights on at 07 h 00 min) with food and water ad libitum. All experiments are carried out by an observer blind to the treatments and in accordance with the Home Office Animals (Scientific Procedures) Act 1986.

Chronic Constriction Injury (CCI) Rat Model of Neuropathic Pain

The CCI of static nerve is performed as previously described by Bennett and Xie (Bennett G J, Xie Y K. A peripheral mononeuropathy in rat that produces disorders of pain sensation like those seen in man. Pain: 33:87–107, 1988). Animals are anaesthetised with a 2% isofluorane/O2 mixture. The right hind thigh is shaved and swabbed with 1% iodine. Animals are then transferred to a homeothermic blanket for the durayion of the procedure and anaesthesia maintained during surgery via a nose cone. The skin is cut along the line of the thighbone. The common sciatic nerve is exposed at the middle of the thigh by blunt dissection through biceps femoris. About 7 mm of nerve is freed proximal to the sciatic trifurcation, by inserting forceps under the nerve and the nerve gently lifted out of the thigh. Suture is pulled under the nerve using forceps and tied in a simple knot until slight resistance is felt and then double knotted. The procedure is repeated until 4 ligatures (4–0 silk) are tied loosely around the nerve with approx 1 mm spacing. The incision is closed in layers and the wound treated with topical antibiotics.

Streptozocin (STZ)—Induced Diabetes Neuropathy in the Rat

Diabetes is induced by a single intraperitoneal injection of streptozotocin (50 mg/kg) freshly dissolved in 0.9% sterile saline. Streptozotocin injection induces a reproducible mechanical allodynia within 3 weeks, lasting for at least 7 weeks (Chen and Pan, Hypersensitivity of Spinothalamic Tract Neurons Associated With Diabetic Neuropathic Pain in Rats. J Neurophysiol 87: 2726–2733, 2002).

Assessment of Static and Dynamic Allodynia

Static Allodynia.

Animals are habituated to wire bottom test cages prior to the assessment of allodynia. Static allodynia is evaluated by application of von Frey hairs (Stoelting, Wood Dale, Ill., USA.) in ascending order of force (0.6, 1, 1.4, 2, 4, 6, 8, 10, 15 and 26 grams) to the plantar surface of hind paws. Each von Frey hair is applied to the paw for a maximum of 6 sec, or until a withdrawal response occurred. Once a withdrawal response to a von Frey hair is established, the paw is re-tested, starting with the filament below the one that produced a withdrawal, and subsequently with the remaining filaments in descending force sequence until no withdrawal occurrs. The highest force of 26 g lifts the paw as well as eliciting a response, thus represented the cut off point. Each animal has both hind paws tested in this manner. The lowest amount of force required to elicit a response is recorded as paw withdrawal threshold (PWT) in grams. Static allodynia is defined as present if animals respond to a stimulus of, or less than, 4 g, which is innocuous in naive rats (Field M J, Bramwell S, Hughes J, Singh L. Detection of static and dynamic components of mechanical allodynia in rat models of neuropathic pain: are they signalled by distinct primary sensory neurones? Pain, 1999; 83:303–11).

Dynamic Allodynia

Dynamic allodynia is assessed by lightly stroking the plantar surface of the hind paw with a cotton bud. To avoid recording general motor activity, care is taken to perform this procedure in fully habituated rats that are not active. At least two measurements are taken at each time point, the mean of which represents the paw withdrawal latency (PWL). If no reaction is exhibited within 15 sec the procedure is terminated and animals are assigned this withdrawal time. A pain withdrawal response is often accompanied with repeated flinching or licking of the paw. Dynamic allodynia is considered to be present if animals respond to the cotton stimulus within 8 sec of commencing stroking (Field et al, 1999).

Nociceptive Pain

The activity of a compound in the treatment of nociceptive pain may be measured according to the following test protocols.

Hotplate

Experimental Procedure: Male Sprague Dawley rats are placed on a hot plate (Ugo Basile, Italy) maintained at 55±5°

C. The time between placement of the animal on the hot plate and occurrence of either licking of fore or hind paw, shaking or jumping off the surface is measured. Baseline measurements are made and animals reassessed following drug administration. The cut off time for hot plate latencies is set at 20 seconds to prevent tissue damage.

Ovariohysterectomy (OVX)

Experimental Procedure: Female Sprague Dawley rats are placed into an anaesthetic chamber and anaesthetised with a 2% isofluorane $O_2$ mixture. During surgery, anaesthesia is maintained via a nose cone. OVX is performed via a midline incision (2 cm in length) in the linea alba, whilst the animal is on a heat blanket. The ovarian ligaments and cervix are ligated with 5–0 silk, using a single clamp technique. The ovaries and uterus are then removed. The abdominal wall is closed using 4 simple interrupted sutures and the skin closed using 4 wound clips. Immediately after surgery animals are placed in individual plexiglass chambers. Once the animal has recovered from the anaesthetic the abdominal body postures are recorded in 30 min bins at various time points. Postures scored are humpback position, contraction of the muscle of the abdomen associated with inward movements of the hind limb, stretching of the body and squashing of the lower abdomen against the floor. Each of these behaviours is scored as one posture.

Brennan

Experimental Procedure: Male Sprague Dawley rats are placed into an anaesthetic chamber and anaesthetised with a 2% isofluorane $O_2$ mixture. During surgery, anaesthesia is maintained via a nose cone. The plantar aspect of the right hind paw is cleaned with 50% ethanol. A 1 cm long longitudinal incision is made with a number 11 blade through the skin and fascia of the plantar aspect of the foot, starting 0.5 cm from the proximal edge of the heel and extending toward the toes. The plantaris muscle is elevated using forceps and incised longitudinally, the muscle origin and insertion remain intact. After haemostasis with gentle pressure, the skin is closed with two simple sutures of braided silk.

Mono-Iodoacetate (MIA)—Induced OA Model

Male 6 weeks-old Sprague-Dawley (SD, Japan SLC or Charles River Japan) rats are anesthetized with pentobarbital. Injection site is shaved and cleaned with 70% ethanol. 25 µl of MIA solution or saline is injected in the right knee joint using a 29G needle. 7, 14, 19 and 20 days after the MIA injection, train rats to measure the weight bearing (WB) without their stress. 21 days after the MIA injection, the WB on two of each hind paw is measured and the WB deficit is calculated. Define the WB deficit value as "pre value". Arrange for experimental group evenly in consideration of pre value and prepre value. After the administration of test compounds or vehicle, the WB on two of each hind paw was measured.

Cancer Pain Model

These experiments use adult male C3H/HeN mice (Nihon SLC, Shizuoka, Japan). The mice are housed in accordance with National Institutes of Health guidelines in a vivarium maintained at 22° C. with a 12-hour alternating light-dark cycle, and were given food and water ad libitum. The sarcoma injection protocol which is used has been described. After induction of general anesthesia with an inhalation of isofluran (2%), a superficial incision is made in the skin overlying the patella, using Mora scissors. The patellar ligament is then cut, exposing the condyles of the distal femur. A 30-gauge needle is inserted at the level of the intercondylar notch and into the medullary canal to create an initial core pathway. After the initial core is made, a 29-gauge needle is used to make the final pathway into the bone. A 0.5-mm depression is then made using a half-round bur in a pneumatic dental high speed handpiece, to serve as mechanical retention for the dental resin plug. Then, 20 µl α-minimum essential media (Sigma; sham injection) or 20 µl media containing $1 \times 10^5$ 2472 osteolytic sarcoma cells (American Type Culture Collection, Rockville, Md.; sarcoma injection) is injected using a 29-gauge needle and a 0.25 cc syringe. To prevent leakage of cells outside the bone, the injection site is closed with dental resin, followed by copious irrigation with filtered water. Wound closure is achieved using auto wound clips (Becton Dickinson, San Jose, Calif.). Wound clips are removed at day 5 to prevent interference with behavioral testing.

Assessment of Static and Dynamic Allodynia

Static Allodynia.

Animals are habituated to wire bottom test cages prior to the assessment of allodynia. Static allodynia is evaluated by application of von Frey hairs (Stoelting, Wood Dale, Ill., USA.) in ascending order of force (0.6, 1, 1.4, 2, 4, 6, 8, 10, 15 and 26 grams) to the plantar surface of hind paws. Each von Frey hair is applied to the paw for a maximum of 6 sec, or until a withdrawal response occurrs. Once a withdrawal response to a von Frey hair is established, the paw is re-tested, starting with the filament below the one that produces a withdrawal, and subsequently with the remaining filaments in descending force sequence until no withdrawal occurs. The highest force of 26 g lifts the paw as well as eliciting a response, thus represents the cut off point. Each animal has both hind paws tested in this manner. The lowest amount of force required to elicit a response is recorded as paw withdrawal threshold (PWT) in grams. Static allodynia is defined as present if animals respond to a stimulus of, or less than, 4 g, which is innocuous in naive rats (Field M J, Bramwell S, Hughes J, Singh L. Detection of static and dynamic components of mechanical allodynia in rat models of neuropathic pain: are they signalled by distinct primary sensory neurones? Pain, 1999; 83:303–11).

Dynamic Allodynia

Dynamic allodynia is assessed by lightly stroking the plantar surface of the hind paw with a cotton bud. To avoid recording general motor activity, care is taken to perform this procedure in fully habituated rats that are not active. At least two measurements are taken at each time point, the mean of which represents the paw withdrawal latency (PWL). If no reaction is exhibited within 15 sec the procedure is terminated and animals are assigned this withdrawal time. A pain withdrawal response is often accompanied with repeated flinching or licking of the paw. Dynamic allodynia is considered to be present if animals respond to the cotton stimulus within 8 sec of commencing stroking (Field et al, 1999).

Radiant Heat Paw Withdrawal

Experimental procedure: Thermal paw withdrawal is assessed using the rat plantar test (Ugo Basile, Italy) following a modified method of Hargreaves et al., 1988. Rats are habituated to the apparatus that consists of three individual perspex boxes on an elevated glass table. A mobile radiant heat source is located under the table and focused onto the hind paw and paw withdrawal latencies (PWL) are recorded. There is an automatic cut off point of 22.5 s to prevent tissue damage. PWL are taken 2–3 times for both hind paws of each animal, the mean of which represents baselines for right and left hind paws. The apparatus is calibrated to give a PWL of approximately 10 s.

Weight Bearing

Experimental procedure: Animals are examined for hypersensitivity in the weight-bearing test, using an "incapacitance tester" (Linton Instruments, Diss, Norfolk, U.K.). Rats were positioned with their fore limbs up on a perspex slope and hind limb weight distribution was measured via force transducers under each of the hind paws. Each animal is placed in the apparatus and the weight load exerted by the hind paws is noted. The difference in weight bearing is calculated by subtracting the ipsilateral (injured) paw from the contralateral paw (normal) and this constitutes the raw data.

Inflammatory Pain

The activity of compound in the treatment of inflammatory pain may be measured according to the following test protocol.

CFA-Induced Weight Bearing Deficits in Rats

Male 7-week-old SD rats are fasted overnight. CFA (300 μg of Mycobacterium Tuberculosis H37 RA (Difco Laboratories) in 100 μL of liquid paraffin (Wako)) is injected into the rat's right hind footpad. Two days after the administration of CFA, the changes in hind paw weight distribution between the left (ipsilateral) and the right (contralateral) limbs are measured as an index of pain by using Linton Incapacitance tester (Linton Instrumentation, UK). The test compound suspended in 0.1% MC (Wako) is administered orally in a volume of 1 mL per 100 g body weight. Each animal is placed in the apparatus and the weight load exerted by the hind paws is measured before, 1, 2 and 4 hours after drug administration.

Carrageenin—Induced Mechanical Hyperalgesia in Rats

Male 4-week-old SD rats are fasted overnight. Hyperalgesia is induced by intraplantar injection of Lambda-carrageenin (0.1 ml of 1% w/v solution in saline, Zushikagaku). The test compound (1 ml of 0.1% methylcellulose/100 g body weight) is given orally at 5.5 hours after the carrageenin injection. The paw withdrawal threshold (gram) is measured by analgesimeter (Ugo Basile) at 3.5, 4.5, 6.5 and 7.5 hours after the carrageenin injection. (Randall L. O. & Selifto I. J., Arch. Int. Pharmacodyn. 111, 409–419, 1957)

Carrageenan-Induced Thermal Hyperalgesia (CITH) in the Rat

Thermal hyperalgesia is assessed using the rat plantar test (Ugo Basile, Comerio, Italy), according to a method modified by Hargreaves et al. (1988). Briefly, rats are habituated to the apparatus that consists of three individual Perspex boxes on a glass table. A mobile radiant heat source is located under the table and focused onto the desired paw. Paw withdrawal latencies (PWLs) are recorded three times for both hind paws of each animal, the mean of which represents baseline for left and right hind paws. The apparatus is calibrated to give a PWL of approximately 10 s in naïve rats. To prevent tissue damage of the plantar zone, a 22.5 sec cut-off is observed. Lambda carrageenan is injected intraplantarly (100 μl, 20 mg/ml) the right hind paw and baseline recordings of PWT are taken 2 hr post administration.

Visceral Pain

The activity of a compound in the treatment of visceral pain may be measured according to the following test protocols.

Several models are available to determine if a compound is effective in treating disorders of the viscera. These models include a LPS model (Eutamene H et al, *J Pharmacol Exp Ther* 2000 295 (1):162–7), a TNBS model (Diop L. et al, Gastroenterology 1999, 116, 4(2): A986), a IBD model (Clemett D, Markham A, *Drugs* 2000 April;59(4):929–56), a pancreatic pain model (Isla A M, *Hosp Med* 2000 June; 61(6):386–9) and a visceral non digestive pain model (Boucher M et al, *J Urol* 2000 July; 164(1):203–8).

TNBS-Induced Chronic Visceral Allodynia in Rats

In this experimental model of colonic distension in awake rats, previous injection of trinitrobenzenesulfonic acid (TNBS) into the proximal colon lowered the visceral pain threshold.

Materials and methods: Male Sprague-Dawley rats are used. The animals are housed 3 per cage in a regulated environment ($20\pm1°$ C., $50\pm5\%$ humidity, with light 8:00 am to 8:00 pm). At day 0, under anesthesia (ketamine 80 mg/kg i.p.; acepromazine 12 mg/kg i.p.), the injection of TNBS (50 mg/kg in ethanol 30%), or saline (1.5 ml/kg) for control rats, is performed into the proximal colon wall (1 cm from the cecum). After the surgery, animals are individually housed in polypropylene cages and kept in a regulated environment ($20\pm1°$ C., $50\pm5\%$ humidity, with light 8:00 a.m. to 8:00 p.m.) during 7 days. At day 7 after TNBS administration, a balloon (5–6 cm length) is inserted by anus, and kept in position (tip of balloon 5 cm from the anus) by taping the catheter to the base of the tail. Oral administration of the test compound is performed 1 h before the colonic distension cycle: the balloon is progressively inflated by steps of 5 mm Hg (0.667 kPa), from 0 to 75 mm Hg, each step of inflation lasting 30 s. Each cycle of colonic distension is controlled by a standard barostat. The threshold (mm Hg) corresponds to the pressure which produced the first abdominal contraction, and the cycle of distension is then discontinued. The colonic threshold is determined after performance of four cycles of distension on the same animal.

LPS-Induced Rectal Hypersensitivity in Rats

Intraperitoneal injection of bacterial lipo-polysaccharide (LPS) has been shown to induce rectal hyperalgesia in awake rats.

Materials and methods: Animals are surgically prepared for electromyography: rats are anaesthetized by intraperitoneal injection of acepromazine (0.6 mg/kg) and ketamine (120 mg/kg). Three groups of three electrodes are implanted in the abdominal external oblique musculature, just superior to the inguinal ligament. Electrodes are exteriorized on the back of the neck and protected by a glass tube attached to the skin. Animals are individually housed in polypropylene cages and kept in a temperature-controlled room (21° C.). Food (UAR pellets, Epinay, France) and water are provided ad libitum.

Electromyographic recordings begin five days after surgery. The electrical activity of abdominal striated muscles is recorded with an electroencephalograph machine (Mini Vil Alvar, Paris, France) using a short time constant (0.03 s) to remove low-frequency signals (<3 Hz) and a paper speed of 3.6 cm/min. Spike bursts are recorded as an index of abdominal contractions.

Distension procedure: Rats are placed in plastic tunnels (6 cm diameter×25 cm long), where they cannot move, escape, or turn around, in order to prevent damage to the balloon. Animals are accustomed to this procedure for four days before rectal distension in order to minimize stress reactions during experiments. The balloon used for distension is an arterial embolectomy catheter (Fogarty, Edwards Laboratories Inc.). Rectal distension is performed by insertion of the balloon (2 mm diameter×2 cm long) into the rectum, at 1 cm from the anus, and catheter is fixed at the base of the tail. It is inflated progressively with tepid water by steps of 0.4 ml, from 0 to 1.2 ml, each step of inflation lasting 5 min. To detect possible leakage, the volume of water introduced in the balloon is checked by complete removal with a syringe at the end of the distension period.

What is claimed is:

1. A compound of Formula (I)

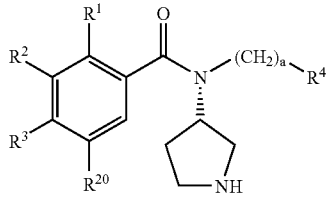

and pharmaceutically and/or veterinarily acceptable salts thereof, wherein:

$R^1$, $R^2$, $R^3$ and $R^{20}$ are each independently H, Cl, Br, F, I, $CF_3$, Me or Et;

$R^4$ is het or $C_{3-7}$ cycloalkyl optionally substituted by $C_{1-4}$ alkyl;

a is 0 or 1; and het is a non-aromatic 5-membered heterocycle which contains at least one N, O or S heteroatom, optionally fused to a 5- or 6-membered carbocyclic group or a second 4-, 5- or 6-membered heterocycle which contains at least one N, O or S heteroatom, wherein the het group is optionally substituted by at least one substituent independently selected from $C_{1-8}$alkyl, $C_{1-8}$alkoxy, OH, halo, $CF_3$, $OCF_3$, $SCF_3$, hydroxy-$C_{1-6}$alkyl, $C_{1-4}$alkoxy-$C_{1-6}$alkyl and $C_{1-4}$alkyl-S—$C_{1-4}$alkyl;

provided that at least one of $R^1$, $R^2$ and $R^3$ is other than H.

2. A compound according to claim 1, wherein:
$R^1$ is Cl, Br, F, I, $CF_3$, Me or Et; and
$R^2$ and $R^3$ are each independently H, Cl, Br, F, I, $CF_3$, Me or Et.

3. A compound according to claim 1, wherein:
$R^1$ and $R^2$ are each independently Cl, Br, F, I, Me or Et; and
$R^3$ is H, Cl, Br, F, I, Me or Et.

4. A compound according to claim 1, wherein:
$R^1$ is Cl, Me or $CF_3$;
$R^2$ is H, Cl or F; and
$R^3$ is H, Cl or F.

5. A compound according to claim 1, wherein $R^4$ is $C_{3-7}$ cycloalkyl.

6. A compound according to claim 1, wherein a is 0.

7. A compound according to claim 1 which is:
2,3-dichloro-N-cyclopentyl-N-[(3S)-pyrrolidin-3-yl]benzamide,
2,3-dichloro-N-cyclopentyl-4-fluoro-N-[(3S)-pyrrolidin-3-yl]benzamide,
3-chloro-N-cyclopentyl-2-methyl-N-[(3S)-pyrrolidin-3-yl]benzamide,
N-cyclopentyl-3-fluoro-2-methyl-N-[(3S)-pyrrolidin-3-yl]benzamide,
2-chloro-N-cyclopentyl-3-fluoro-N-[(3S)-pyrrolidin-3-yl]benzamide,
2,3-dichloro-N-cyclohexyl-N-[(3S)-pyrrolidin-3-yl]benzamide,
2-chloro-N-cyclohexyl-3-fluoro-N-[(3S)-pyrrolidin-3-yl]benzamide,
N-cyclohexyl-3-fluoro-2-methyl-N-[(3S)-pyrrolidin-3-yl]benzamide,
2,3-dichloro-N-cyclobutyl-N-[(3S)-pyrrolidin-3-yl]benzamide,
N-cyclobutylmethyl-2,3-dichloro-N-[(3S)-pyrrolidin-3-yl]benzamide,
2,3-dichloro-N-(cyclopropylmethyl)-N-[(3S)-pyrrolidin-3-yl]benzamide,
2chloro-N-cyclopentyl-N[(3S)-pyrrolidin-3-yl]benzamide,
2chloro-N-cyclohexyl-N-[(3S)-pyrrolidin-3-yl]benzamide,
2chloro-N-cycloheptyl-N-[(3S)-pyrrolidin-3yl]benzamide,
N-cycloheptyl-N-[(3S)-pyrrolidin-3-yl]-2-(trifluoromethyl)benzamide,
N-cyclohexyl-N-[(3S)-pyrrolidin-3-yl]-2-(trifluoromethyl)benzamide,
N-cyclopentyl-N-[(3S)-pyrrolidin-3-yl]-2-(trifluoromethyl)benzamide,
2,3-Dichloro-N-[(1-methylcyclopropyl)methyl]-N-[(3S)-pyrrolidin-3-yl]benzamide,
3-Chloro-2-methyl-N-[(1-methylcyclopropyl)methyl]-N-[(3S)-pyrrolidin-3yl]benzamide, and
N-(cyclobutylmethyl)-N-[(3S)-pyrrolidin-3-yl]-2-(trifluoromethyl)benzamide, or pharmaceutically and/or veterinarily acceptable salts thereof.

8. A compound according to claim 7 which is 2,3-dichloro-N-cyclopentyl-N-[(3S)-pyrrolidin-3-yl]benzamide, or pharmaceutically and/or veterinarily acceptable salts thereof.

9. A pharmaceutical composition comprising a compound as claimed in claim 1 and a pharmaceutically acceptable adjuvant, diluent or carrier.

10. A method of treatment of urinary disorders, depression, pain, premature ejaculation, ADHD or fibromyalgia, which comprises administering a therapeutically effective amount of a compound according to claim 1 to a patient in need of such treatment.

11. A method according to claim 10, wherein the urinary disorder is urinary incontinence.

12. A process for preparing a compound according to claim 1 which comprises reacting a compound of formula (IX):

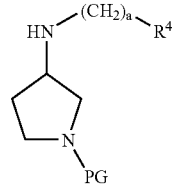

wherein $R^4$ and a are as defined in claim 1 and PG is a protecting group, with an acid or acyl halide of Formula (II):

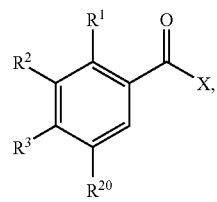

wherein X is OH or halo, and deprotecting.

* * * * *